United States Patent
Chen et al.

(10) Patent No.: US 8,772,505 B2
(45) Date of Patent: Jul. 8, 2014

(54) ANTIVIRAL COMPOUNDS COMPOSED OF THREE ALIGNED ARYL MOIETIES TO TREAT DISEASES SUCH AS HEPATITIS C

(75) Inventors: Kevin X. Chen, Edison, NJ (US); Anilkumar Gopinadhan Nair, Edison, NJ (US); Qingbei Zeng, Edison, NJ (US); Stuart B. Rosenblum, West Orange, NJ (US); Joseph A. Kozlowski, Princeton, NJ (US); F. George Njoroge, Warren, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 55 days.

(21) Appl. No.: 13/375,088

(22) PCT Filed: May 28, 2010

(86) PCT No.: PCT/US2010/036520
§ 371 (c)(1),
(2), (4) Date: Jun. 11, 2012

(87) PCT Pub. No.: WO2010/138790
PCT Pub. Date: Dec. 2, 2010

(65) Prior Publication Data
US 2013/0164258 A1    Jun. 27, 2013

Related U.S. Application Data

(60) Provisional application No. 61/182,375, filed on May 29, 2009, provisional application No. 61/243,728, filed on Sep. 18, 2009.

(51) Int. Cl.
*A61K 31/4418* (2006.01)
*A61K 31/4184* (2006.01)
*C07D 403/14* (2006.01)
*C07D 401/14* (2006.01)

(52) U.S. Cl.
USPC ............... 548/306.1; 548/304.7; 546/273.4; 514/338; 514/394

(58) Field of Classification Search
USPC .......... 548/304.7, 306.1; 546/273.4; 514/338, 514/394
See application file for complete search history.

(56) References Cited

U.S. PATENT DOCUMENTS

| | | | |
|---|---|---|---|
| 5,935,982 A | 8/1999 | Dykstra et al. |
| 7,438,920 B1 | 10/2008 | Kim et al. |
| 7,659,270 B2 | 2/2010 | Bachand et al. |
| 7,906,655 B2 | 3/2011 | Belema et al. |
| 8,147,818 B2 | 4/2012 | Bachand et al. |
| 8,303,944 B2 | 11/2012 | Bachand et al. |
| 8,420,686 B2 | 4/2013 | Or et al. |
| 8,426,458 B2 | 4/2013 | Or et al. |

| | | | |
|---|---|---|---|
| 2006/0019974 A1 | 1/2006 | Mederski et al. |
| 2007/0032497 A1 | 2/2007 | Hahimoto et al. |
| 2007/0049593 A1 | 3/2007 | Oka et al. |

(Continued)

FOREIGN PATENT DOCUMENTS

| | | |
|---|---|---|
| WO | 0020400 | 4/2000 |
| WO | 2010065681 | 6/2010 |
| WO | 2010096777 | 8/2010 |
| WO | 2010138790 | 12/2010 |
| WO | 2011075439 | 6/2011 |

OTHER PUBLICATIONS

U.S. Appl. No. 13/375,094, Qingbei et al., filed Jun. 11, 2012.*

(Continued)

*Primary Examiner* — Yong Chu
*Assistant Examiner* — Sonya Wright
(74) *Attorney, Agent, or Firm* — Jeffrey P. Bergman; Sheldon O. Heber

(57) ABSTRACT

The present invention relates to novel Tricyclic Compounds, compositions comprising at least one Tricyclic Compound, and methods of using Tricyclic Compounds for treating or preventing a viral infection or a virus-related disorder in a patient. The present invention provides Tricyclic Compounds of Formula (I): Non-limiting examples of the Compounds of Formula (I) include compound 44 The Compounds of Formula (II) can be useful for inhibiting HCV viral replication or replicon activity, and for treating or preventing HCV infection in a patient.

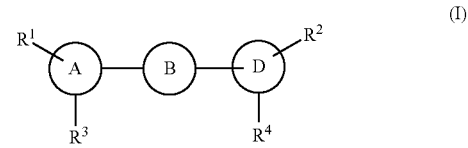

(I)

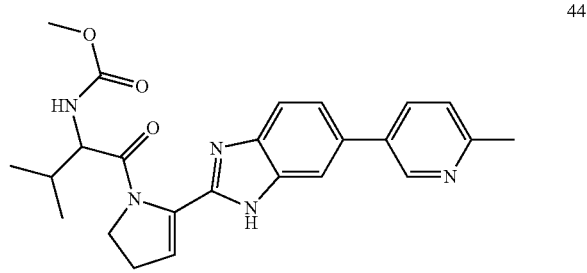

44

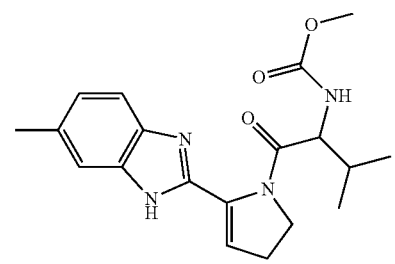

14 Claims, No Drawings

(56) References Cited

U.S. PATENT DOCUMENTS

| | | |
|---|---|---|
| 2007/0185175 A1 | 8/2007 | Liu et al. |
| 2008/0044379 A1 | 2/2008 | Bachand et al. |
| 2008/0200423 A1 | 8/2008 | Cook et al. |
| 2008/0311075 A1* | 12/2008 | Bachand et al. ............ 424/85.2 |
| 2009/0202478 A1 | 8/2009 | Bachand et al. |
| 2009/0202483 A1 | 8/2009 | Bachand et al. |
| 2010/0055071 A1 | 3/2010 | Leivers et al. |
| 2010/0087382 A1 | 4/2010 | Bailey et al. |
| 2010/0233122 A1 | 9/2010 | Qiu et al. |
| 2010/0316607 A1 | 12/2010 | Or et al. |
| 2011/0223134 A1 | 9/2011 | Nair et al. |
| 2012/0083483 A1 | 4/2012 | Coburn et al. |
| 2012/0251491 A1 | 10/2012 | Rosenblum et al. |
| 2012/0258078 A1 | 10/2012 | Rosenblum et al. |
| 2012/0276047 A1 | 11/2012 | Rosenblum et al. |
| 2013/0156731 A1 | 6/2013 | Chen et al. |

OTHER PUBLICATIONS

Wachowius et al. Synthesis and DNA duplex recognition of a triplex-forming oligonucleotide with an ureide-substituted 4-phenylimidazole nucleoside. Tetrahedron Letters 2008, 49:7264-7267.

Pujals et al. "Replacement of a proline with a silaproline causes a 20-fold increase in the cellular uptake of a Pro-Rich Peptide." J. Am. Chem. Soc. 2006, 128:8479-8483.

Uwe Koch and Frank Narjes: "Recent Progress in the Development of Inhibitors of the Hepatitis C Virus RNA-Dependent RNA Polymerase" Current Topics in Medicinal Chemistry, Bentham Science Publishers Ltd, Netherlands, vol. 7, Jan. 1, 2007 (Jan. 1, 2007), pp. 1302-1329.

* cited by examiner

ANTIVIRAL COMPOUNDS COMPOSED OF THREE ALIGNED ARYL MOIETIES TO TREAT DISEASES SUCH AS HEPATITIS C

CROSS-REFERENCE TO RELATED APPLICATIONS

This application is the national stage application under 35 U.S.C. 371 of International Patent Application No. PCT/US2010/036520, filed May 28, 2010, which claims priority to U.S. Provisional Application No. 61/182,375, filed May 29, 2009 and U.S. Provisional Application No. 61/243,728, filed Sep. 18, 2009. Each of the aforementioned PCT and priority applications is incorporated by reference in its entirety.

REFERENCE TO SEQUENCE LISTING SUBMITTED ELECTRONICALLY

The sequence listing of the present application is submitted electronically via EFS-Web as an ASCII formatted sequence listing with a file name "IN2009.6981-US-PCT_SEQ.LIST.TXT," creation date of Jan. 30, 2012, and a size of 1 KB. This sequence listing submitted via EFS-Web is part of the specification and is herein incorporated by reference in its entirety.

FIELD OF THE INVENTION

The present invention relates to novel Tricyclic Compounds, compositions comprising at least one Tricyclic Compound, and methods of using Tricyclic Compounds for treating or preventing HCV infection in a patient.

BACKGROUND OF THE INVENTION

Hepatitis C virus (HCV) is a major human pathogen. A substantial fraction of these HCV-infected individuals develop serious progressive liver disease, including cirrhosis and hepatocellular carcinoma, which are often fatal. HCV is a (+)-sense single-stranded enveloped RNA virus that has been implicated as the major causative agent in non-A, non-B hepatitis (NANBH), particularly in blood-associated NANBH (BB-NANBH) (see, International Publication No. WO 89/04669 and European Patent Publication No. EP 381 216). NANBH is to be distinguished from other types of viral-induced liver disease, such as hepatitis A virus (HAV), hepatitis B virus (HBV), delta hepatitis virus (HDV), cytomegalovirus (CMV) and Epstein-Barr virus (EBV), as well as from other forms of liver disease such as alcoholism and primary biliar cirrhosis.

It is well-established that persistent infection of HCV is related to chronic hepatitis, and as such, inhibition of HCV replication is a viable strategy for the prevention of hepatocellular carcinoma. Current therapies for HCV infection include α-interferon monotherapy and combination therapy comprising α-interferon and ribavirin. These therapies have been shown to be effective in some patients with chronic HCV infection, but suffer from poor efficacy and unfavorable side-effects and there are currently efforts directed to the discovery of HCV replication inhibitors that are useful for the treatment and prevention of HCV related disorders.

Current research efforts directed toward the treatment of HCV includes the use of antisense oligonucleotides, free bile acids (such as ursodeoxycholic acid and chenodeoxycholic acid) and conjugated bile acids (such as tauroursodeoxycholic acid). Phosphonoformic acid esters have also been proposed as potentially useful for the treatment of various viral infections, including HCV. Vaccine development, however, has been hampered by the high degree of viral strain heterogeneity and immune evasion and the lack of protection against reinfection, even with the same inoculum.

In light of these treatment hurdles, the development of small-molecule inhibitors directed against specific viral targets has become a major focus of anti-HCV research. The determination of crystal structures for NS3 protease, NS3 RNA helicase, NS5A, and NS5B polymerase, with and without bound ligands, has provided important structural insights useful for the rational design of specific inhibitors.

Recent attention has been focused toward the identification of inhibitors of HCV NS5A. HCV NS5A is a 447 amino acid phosphoprotein which lacks a defined enzymatic function. It runs as 56 kd and 58 kd bands on gels depending on phosphorylation state (Tanji, et al. *J. Virol.* 69:3980-3986 (1995)). HCV NS5A resides in replication complex and may be responsible for the switch from replication of RNA to production of infectious virus (Huang, Y, et al., *Virology* 364:1-9 (2007)).

Multicyclic HCV NS5A inhibitors have been reported. See U.S. Patent Publication Nos. US20080311075, US20080044379, US20080050336, US20080044380, US20090202483 and US2009020478.

Other NS5A inhibitors and their use for reducing viral load in HCV infected humans have been described in U.S. Patent Publication No. US20060276511.

Despite the intensive effort directed at the treatment and prevention of HCV and related viral infections, there exists a need in the art for non-peptide, small-molecule compounds having desirable or improved physicochemical properties that are useful for inhibiting viruses and treating viral infections and virus-related disorders. This invention addresses that need.

SUMMARY OF THE INVENTION

In one aspect, the present invention provides Compounds of Formula (I) (herein referred to as the "Tricyclic Compounds") and pharmaceutically acceptable salts thereof:

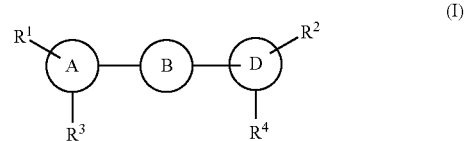

wherein:

A is a 9- to 10-membered bicyclic heteroaryl containing one N atom and optionally, one to two additional heteroatoms independently selected from the group consisting of N, O, and S, wherein A is substituted on one ring carbon atom with $R^3$, and wherein A is optionally substituted on one to two ring carbon atoms with $R^{3a}$ and is optionally substituted on one ring nitrogen atom with $R^1$;

B is a ring selected from the group consisting of:

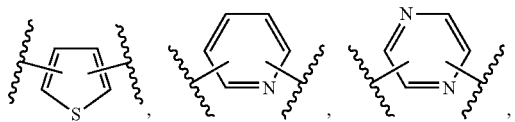

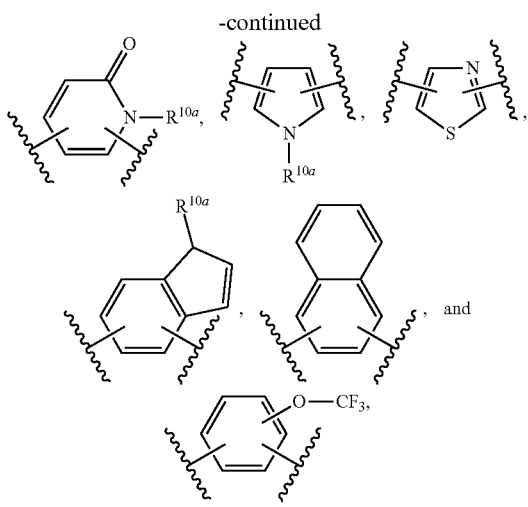

wherein B is optionally substituted on one or more ring carbon atoms by one to three $R^{10}$; and wherein when B is

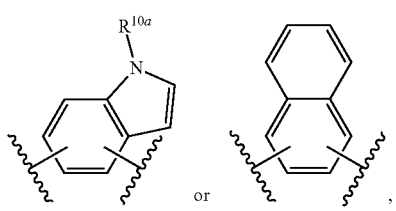

then A and D are each bonded to a common ring of B;

D is a 9 to 10-membered bicyclic heteroaryl containing one N atom and optionally, one to two additional heteroatoms independently selected from the group consisting of N, O, and S, wherein D is substituted on one ring carbon atom with $R^4$, and wherein D is optionally substituted on one two carbon atoms with $R^{4a}$ and is optionally substituted on one ring nitrogen atom with $R^2$;

$R^3$ and $R^4$ are independently selected from the group consisting of:

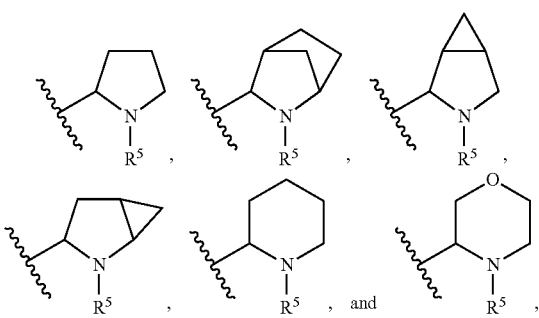

wherein $R^3$ and $R^4$ are optionally and independently substituted with:
(a) one to two fluorine or $C_1$-$C_3$ alkyl;
(b) and one to seven $^2H$;

each occurrence of $R^{3a}$ and $R^{4a}$ is independently selected from the group consisting of H, $C_1$-$C_3$; alkyl, $C_1$-$C_3$ alkoxy, halo, and $C_1$-$C_3$ trifluoroalkoxy;

$R^1$ and $R^2$ are independently H or $C_1$-$C_3$ alkyl;

each occurrence of $R^5$ is independently selected from the group consisting of:
(a) —C(O)—($C_1$-$C_6$ alkyl) optionally substituted by one to eight $R^{12}$ groups, wherein $R^{12}$ is selected from the group consisting of:
  (i) $C_1$-$C_3$ alkoxy,
  (ii) phenyl, optionally substituted by one to four halo, $C_1$-$C_3$ alkyl, or $C_1$-$C_3$; alkoxy;
  (iii) amino,
  (iv) $C_1$-$C_3$; monoalkylamino,
  (v) $C_1$-$C_3$ dialkylamino,
  (vi) —NHC(O)—O—($C_1$-$C_6$ alkyl),
  (vii) —N($C_1$-$C_3$ alkyl)-C(O)—O—($C_1$-$C_6$ alkyl),
  (viii) $C_1$-$C_3$ fluoroalkyl,
  (ix) $C_2$-$C_6$ alkynyl,
  (x) $C_3$-$C_7$ cycloalkyl,
  (xi) pyrrolidinyl,
  (xii) piperidinyl,
  (xiii) pyranyl; and
  (xiv) $^2H$;
(b)

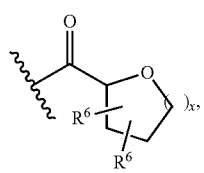

wherein x is 1 or 2, and each occurrence of $R^6$ is independently selected from the group consisting of H, $C_1$-$C_3$ alkyl, $C_1$-$C_3$ alkoxy, and fluoro; and
(c) H;

each occurrence of $R^{10}$ is independently $^2H$, halo, $C_1$-$C_6$ alkyl, $C_1$-$C_6$ alkenyl, $C_1$-$C_6$ alkynyl, $C_1$-$C_6$ alkoxy, cyano, and phenyl; and $R^{10a}$ is H or $C_1$-$C_6$ alkyl.

The Compounds of Formula (I) (also referred to herein as the "Tricyclic Compounds") and pharmaceutically acceptable salts thereof can be useful, for example, for inhibiting HCV viral replication or replicon activity, and for treating or preventing HCV infection in a patient.

The Tricyclic Compounds or pharmaceutically acceptable salts thereof can also be useful for treating or preventing HCV infection in a patient.

Accordingly, the present invention provides methods for treating or preventing HCV infection in a patient, comprising administering to the patient an effective amount of at least one Tricyclic Compound.

The present invention also provides pharmaceutical compositions comprising an effective amount of at least one Tricyclic Compound or a pharmaceutically acceptable salt thereof, and a pharmaceutically acceptable carrier. The compositions can be useful for treating or preventing HCV infection in a patient.

Other embodiments of the present invention include the following:
(a) A pharmaceutical composition comprising an effective amount of a Compound of Formula (I) and a pharmaceutically acceptable carrier.
(b) The pharmaceutical composition of (a), further comprising a second therapeutic agent selected from the group consisting of HCV antiviral agents, immunomodulators, and anti-infective agents.

(c) The pharmaceutical composition of (b), wherein the HCV antiviral agent is an antiviral selected from the group consisting of HCV protease inhibitors and HCV NS5B polymerase inhibitors.

(d) A pharmaceutical combination that is (i) a Compound of Formula (I) and (ii) a second therapeutic agent selected from the group consisting of HCV antiviral agents, immunomodulators, and anti-infective agents; wherein the Compound of Formula (I) and the second therapeutic agent are each employed in an amount that renders the combination effective for inhibiting HCV NS5A, or for treating HCV infection and/or reducing the likelihood or severity of symptoms of HCV infection.

(e) The combination of (d), wherein the HCV antiviral agent is an antiviral selected from the group consisting of HCV protease inhibitors and HCV NS5B polymerase inhibitors.

(f) A method of inhibiting HCV NS5A in a subject in need thereof which comprises administering to the subject an effective amount of a Compound of Formula (I).

(g) A method of treating HCV infection and/or reducing the likelihood or severity of symptoms of HCV infection in a subject in need thereof which comprises administering to the subject an effective amount of a Compound of Formula (I).

(h) The method of (g), wherein the Compound of Formula (I) is administered in combination with an effective amount of at least one second therapeutic agent selected from the group consisting of HCV antiviral agents, immunomodulators, and anti-infective agents.

(i) The method of (h), wherein the HCV antiviral agent is an antiviral selected from the group consisting of HCV protease inhibitors and HCV NS5B polymerase inhibitors.

(j) A method of inhibiting HCV NS5A in a subject in need thereof which comprises administering to the subject the pharmaceutical composition of (a), (b), or (c) or the combination of (d) or (e).

(k) A method of treating HCV infection and/or reducing the likelihood or severity of symptoms of HCV infection in a subject in need thereof which comprises administering to the subject the pharmaceutical composition of (a), (b), or (c) or the combination of (d) or (e).

The present invention also includes a compound of the present invention for use (i) in, (ii) as a medicament for, or (iii) in the preparation of a medicament for:

(a) inhibiting HCV NS5A, or (b) treating HCV infection and/or reducing the likelihood or severity of symptoms of HCV infection. In these uses, the compounds of the present invention can optionally be employed in combination with one or more second therapeutic agents selected from HCV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

In the embodiments of the compound provided above, it is to be understood that each embodiment may be combined with one or more other embodiments, to the extent that such a combination provides a stable compound and is consistent with the description of the embodiments. It is further to be understood that the embodiments of compositions and methods provided as (a) through (k) above are understood to include all embodiments of the compounds, including such embodiments as result from combinations of embodiments.

The details of the invention are set forth in the accompanying detailed description below.

Although any methods and materials similar to those described herein can be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention provides Tricyclic Compounds, pharmaceutical compositions comprising at least one Tricyclic Compound, and methods of using the Tricyclic Compounds for treating or preventing a viral infection or a virus-related disorder in a patient.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc. . . .

As used herein, and throughout this disclosure, the following terms, unless otherwise indicated, shall be understood to have the following meanings:

A "patient" is a human or non-human mammal. In one embodiment, a patient is a human. In another embodiment, a patient is a chimpanzee.

The term "effective amount" as used herein, refers to an amount of Tricyclic Compound and/or an additional therapeutic agent, or a composition thereof that is effective in producing the desired therapeutic, ameliorative, inhibitory or preventative effect when administered to a patient suffering from HCV infection. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HCV viral infection or HCV-virus related disorder, refers to reducing the likelihood of HCV infection.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In another embodiment, an alkyl group contains from about 1 to about 6 carbon atoms. Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH₂, —NH(alkyl), —N(alkyl)₂, —NH(cycloalkyl), —O—C(O)-alkyl, —O—C(O)-aryl, —O—C(O)-cycloalkyl, —C(O)OH and —C(O)O-alkyl. In one embodiment, an alkyl group is unsubstituted. In another embodiment, an alkyl group is linear. In another embodiment, an alkyl group is branched. The term "$C_1$-$C_6$ alkyl" refers to an alkyl group having from 1 to 6 carbon atoms. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH₂, —NH(alkyl), —N(alkyl)₂, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH₂, —NH(alkyl), —N(alkyl)₂, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —CH₂—, —CH₂CH₂—, —CH₂CH₂CH₂—, —CH₂CH₂CH₂CH₂—, —CH(CH₃)CH₂CH₂—, —CH(CH₃)— and —CH₂CH(CH₃)CH₂—. In one embodiment, an alkylene group has from 1 to about 6 carbon atoms. In another embodiment, an alkylene group is branched. In another embodiment, an alkylene group is linear. In one embodiment, an alkylene group is —CH₂—. The term "$C_1$-$C_6$ alkylene" refers to an alkylene group having from 1 to 6 carbon atoms. Unless otherwise indicated, an alkylene group is unsubstituted.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "arylene," as used herein, refers to a bivalent group derived from an aryl group, as defined above, by removal of a hydrogen atom from a ring carbon of an aryl group. An arylene group can be derived from a monocyclic or multicyclic ring system comprising from about 6 to about 14 carbon atoms. In one embodiment, an arylene group contains from about 6 to about 10 carbon atoms. In another embodiment, an arylene group is a naphthylene group. In another embodiment, an arylene group is a phenylene group. An arylene group can be optionally substituted with one or more "ring system substituents" which may be the same or different, and are as defined herein below. An arylene group is divalent and either available bond on an arylene group can connect to either group flanking the arylene group. For example, the group "A-arylene-B," wherein the arylene group is:

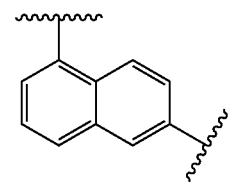

is understood to represent both:

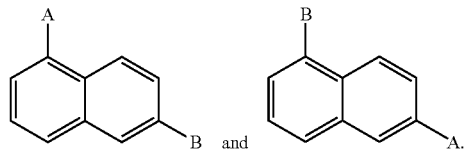

In one embodiment, an arylene group can be optionally fused to a cycloalkyl or cycloalkanoyl group. Unless otherwise indicated, an arylene group is unsubstituted. Non-limiting examples of arylene groups include phenylene and naphthalene. In another embodiment, an arylene group is:

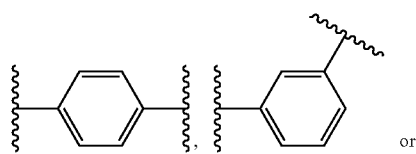

or

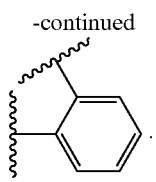

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. The term "3 to 7-membered cycloalkyl" refers to a cycloalkyl group having from 3 to 7 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

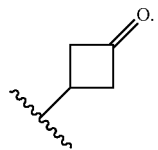 [SMILES: *C1CC(=O)C1]

The term "cycloalkenyl," as used herein, refers to a non-aromatic mono- or multicyclic ring system comprising from about 4 to about 10 ring carbon atoms and containing at least one endocyclic double bond. In one embodiment, a cycloalkenyl contains from about 4 to about 7 ring carbon atoms. In another embodiment, a cycloalkenyl contains 5 or 6 ring atoms. Non-limiting examples of monocyclic cycloalkenyls include cyclopentenyl, cyclohexenyl, cyclohepta-1,3-dienyl, and the like. A cycloalkenyl group can be optionally substituted with one or more "ring system substituents" which may be the same or different, and are as defined herein below. A ring carbon atom of a cycloalkyl group may be functionalized as a carbonyl group. In one embodiment, a cycloalkenyl group is cyclopentenyl. In another embodiment, a cycloalkenyl group is cyclohexenyl. The term "4 to 7-membered cycloalkenyl" refers to a cycloalkenyl group having from 4 to 7 ring carbon atoms. Unless otherwise indicated, a cycloalkenyl group is unsubstituted.

The term "halo," as used herein, means —F, —Cl, —Br or —I. In one embodiment, a halo group is —F or —Cl. In another embodiment, a halo group is —F.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —CH$_2$F, —CHF$_2$, —CF$_3$, —CH$_2$Cl and —CCl$_3$. The term "C$_1$-C$_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$OH and —CH$_2$CH(OH)CH$_3$. The term "C$_1$-C$_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered heteroaryl. In another embodiment, a heteroaryl group comprises a 5 to 6-membered heteroaryl group fused to a benzene ring. The term "3 to 7-membered cycloalkyl" refers to a cycloalkyl group having from 3 to 8 ring carbon atoms. Unless otherwise indicated, a heteroaryl group is unsubstituted.

The term "heteroarylene," as used herein, refers to a bivalent group derived from an heteroaryl group, as defined above, by removal of a hydrogen atom from a ring carbon or ring heteroatom of a heteroaryl group. A heteroarylene group can be derived from a monocyclic or multicyclic ring system comprising about 5 to about 14 ring atoms, wherein from 1 to 4 of the ring atoms are each independently O, N or S and the remaining ring atoms are carbon atoms. A heteroarylene group can be optionally substituted by one or more "ring system substituents" which may be the same or different, and are as defined herein below. A heteroarylene group is joined via a ring carbon atom or by a nitrogen atom with an open valence, and any nitrogen atom of a heteroarylene can be optionally oxidized to the corresponding N-oxide. The term "heteroarylene" also encompasses a heteroarylene group, as defined above, which is fused to a benzene ring. Non-limiting examples of heteroarylenes include pyridylene, pyrazinylene, furanylene, thienylene, pyrimidinylene, pyridonylene (including those derived from N-substituted pyridonyls), isoxazolylene, isothiazolylene, oxazolylene, oxadiazolylene, thiazolylene, pyrazolylene, thiophenylene, furazanylene, pyrrolylene, triazolylene, 1,2,4-thiadiazolylene, pyrazinylene, pyridazinylene, quinoxalinylene, phthalazinylene, oxindolylene, imidazo[1,2-a]pyridinylene, imidazo[2,1-b] thiazolylene, benzofurazanylene, indolylene, azaindolylene, benzimidazolylene, benzothienylene, quinolinylene, imidazolylene, benzimidazolylene, thienopyridylene, quinazolinylene, thienopyrimidylene, pyrrolopyridylene, imidazopyridylene, isoquinolinylene, benzoazaindolylene, 1,2,4-triazinylene, benzothiazolylene and the like, and all isomeric forms thereof. The term "heteroarylene" also refers to partially saturated heteroarylene moieties such as, for example, tetrahydroisoquinolylene, tetrahydroquinolylene, and the like. A heteroarylene group is divalent and either available bond on a heteroarylene ring can connect to either group flanking the heteroarylene group. For example, the group "A-heteroarylene-B," wherein the heteroarylene group is:

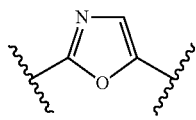 [SMILES: *c1cnc(*)o1]

is understood to represent both:

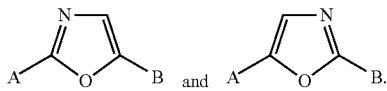

In one embodiment, a heteroarylene group is a monocyclic heteroarylene group or a bicyclic heteroarylene group. In another embodiment, a heteroarylene group is a monocyclic heteroarylene group. In another embodiment, a heteroarylene group is a bicyclic heteroarylene group. In still another embodiment, a heteroarylene group has from about 5 to about 10 ring atoms. In another embodiment, a heteroarylene group is monocyclic and has 5 or 6 ring atoms. In another embodiment, a heteroarylene group is bicyclic and has 9 or 10 ring atoms. In another embodiment, a heteroarylene group is a 5-membered monocyclic heteroarylene. In another embodiment, a heteroarylene group is a 6-membered monocyclic heteroarylene. In another embodiment, a bicyclic heteroarylene group comprises a 5 or 6-membered monocyclic heteroarylene group fused to a benzene ring. Unless otherwise indicated, a heteroarylene group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from about 3 to about 7 ring atoms. In another embodiment, a heterocycloalkyl group is monocyclic has from about 4 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone and the like, and all isomers thereof.

A ring carbon atom of a heterocycloalkyl group may be functionalized as a carbonyl group. An illustrative example of such a heterocycloalkyl group is:

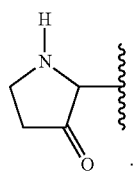

In one embodiment, a heterocycloalkyl group is a 5-membered monocyclic heterocycloalkyl. In another embodiment, a heterocycloalkyl group is a 6-membered monocyclic heterocycloalkyl. The term "3 to 7-membered monocyclic cycloalkyl" refers to a monocyclic heterocycloalkyl group having from 3 to 7 ring atoms. The term "4 to 7-membered monocyclic cycloalkyl" refers to a monocyclic heterocycloalkyl group having from 4 to 7 ring atoms. The term "7 to 11-membered bicyclic cycloalkyl" refers to a bicyclic heterocycloalkyl group having from 7 to 11 ring atoms. Unless otherwise indicated, a heterocycloalkyl group is unsubstituted.

The term "heterocycloalkenyl," as used herein, refers to a heterocycloalkyl group, as defined above, wherein the heterocycloalkyl group contains from 4 to 10 ring atoms, and at least one endocyclic carbon-carbon or carbon-nitrogen double bond. A heterocycloalkenyl group can be joined via a ring carbon, a ring silicon atom or ring nitrogen atom. In one embodiment, a heterocycloalkenyl group has from 4 to 7 ring atoms. In another embodiment, a heterocycloalkenyl group is monocyclic and has 5 or 6 ring atoms. In another embodiment, a heterocycloalkenyl group is bicyclic. A heterocycloalkenyl group can optionally substituted by one or more ring system substituents, wherein "ring system substituent" is as defined above. The nitrogen or sulfur atom of the heterocycloalkenyl can be optionally oxidized to the corresponding N-oxide, S-oxide or S,S-dioxide. Non-limiting examples of heterocycloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluoro-substituted dihydrofuranyl, 7-oxabicyclo[2.2.1]heptenyl, dihydrothiophenyl, dihydrothiopyranyl, and the like and the like. A ring carbon atom of a heterocycloalkenyl group may be functionalized as a carbonyl group. In one embodiment, a heterocycloalkenyl group is a 5-membered heterocycloalkenyl. In another embodiment, a heterocycloalkenyl group is a 6-membered heterocycloalkenyl. The term "4 to 7-membered heterocycloalkenyl" refers to a heterocycloalkenyl group having from 4 to 7 ring atoms. Unless otherwise indicated, a heterocycloalkenyl group is unsubstituted.

The term "ring system substituent," as used herein, refers to a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O-alkylene-aryl, acyl, —C(O)-aryl, halo, —NO$_2$, —CN, —SF$_5$, —C(O)OH, —C(O)O-alkyl, —C(O)O-aryl, —C(O)O-alkylene-aryl, —S(O)—alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, —S(O)$_2$-alkylene-aryl, —S(O)$_2$-alkylene-heteroaryl, cycloalkyl, heterocycloalkyl, —O—C(O)-alkyl, —O—C(O)—aryl, —O—C(O)-cycloalkyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, and Y$_1$Y$_2$NS(O)$_2$—, wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

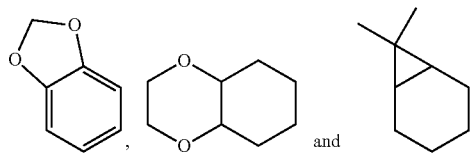

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any variable (e.g., aryl, heterocycle, R$^2$, etc.) occurs more than one time in any constituent or in Formula (I), its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a Tricyclic Compound or a pharmaceutically acceptable salt, hydrate or solvate of the compound. The transformation may occur by various mechanisms (e.g., by metabolic or chemical processes), such as, for example, through hydrolysis in blood.

For example, if a Tricyclic Compound or a pharmaceutically acceptable salt, hydrate or solvate of the compound contains a carboxylic acid functional group, a prodrug can comprise an ester formed by the replacement of the hydrogen atom of the acid group with a group such as, for example, (C$_1$-C$_8$)alkyl, (C$_2$-C$_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—(C$_1$-C$_2$)alkylamino(C$_2$-C$_3$)alkyl (such as β-dimethylaminoethyl), carbamoyl-(C$_1$-C$_2$)alkyl, N,N-di(C$_1$-C$_2$)alkylcarbamoyl-(C$_1$-C$_2$)alkyl and piperidino-, pyrrolidino- or morpholino(C$_2$-C$_3$) alkyl, and the like.

Similarly, if a Tricyclic Compound contains an alcohol functional group, a prodrug can be formed by the replacement of the hydrogen atom of the alcohol group with a group such as, for example, (C$_1$-C$_6$)alkanoyloxymethyl, 1-((C$_1$-C$_6$)alkanoyloxy)ethyl, 1-methyl-1-((C$_1$-C$_6$)alkanoyloxy)ethyl, (C$_1$-C$_6$)alkoxycarbonyloxymethyl, N—(C$_1$-C$_6$)alkoxycarbonylaminomethyl, succinoyl, (C$_1$-C$_6$)alkanoyl, α-amino(C$_1$-C$_4$)alkyl, α-amino(C$_1$-C$_4$)alkylene-aryl, arylacyl and α-aminoacyl, or α-aminoacyl-α-aminoacyl, where each α-aminoacyl group is independently selected from the naturally occurring L-amino acids, —P(O)(OH)$_2$, —P(O)(O(C$_1$-C$_6$)alkyl)$_2$ or glycosyl (the radical resulting from the removal of a hydroxyl group of the hemiacetal form of a carbohydrate), and the like.

If a Tricyclic Compound incorporates an amine functional group, a prodrug can be formed by the replacement of a hydrogen atom in the amine group with a group such as, for example, R-carbonyl-, RO-carbonyl-, NRR'-carbonyl- wherein R and R' are each independently $(C_1-C_{10})$alkyl, $(C_3-C_7)$ cycloalkyl, benzyl, a natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl; carboxy $(C_1-C_6)$alkyl; amino$(C_1-C_4)$alkyl or mono-N— or di-N,N—$(C_1-C_6)$alkylaminoalkyl; —C(Y$^4$)Y$^5$ wherein Y$^4$ is H or methyl and Y$^5$ is mono-N— or di-N,N—$(C_1-C_6)$alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (for example, methyl, ethyl, n-propyl, isopropyl, t-butyl, sec-butyl or n-butyl), alkoxy-alkyl (for example, methoxymethyl), aralkyl (for example, benzyl), aryloxyalkyl (for example, phenoxymethyl), aryl (for example, phenyl optionally substituted with, for example, halogen, $C_{1-4}$ alkyl, or —O—$C_{1-4}$ alkyl or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Tricyclic Compounds can form salts which are also within the scope of this invention. Reference to a Tricyclic Compound herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Tricyclic Compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a Tricyclic Compound with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the Tricyclic Compounds may be atropisomers (e.g., substituted biaryls) and are considered as part of this invention. Enantiomers can also be directly separated using chiral chromatographic techniques.

It is also possible that the Tricyclic Compounds may exist in different tautomeric forms, and all such forms are embraced within the scope of the invention. For example, all keto-enol and imine-enamine forms of the compounds are included in the invention. It should also be noted that tautomeric forms such as, for example, the moieties:

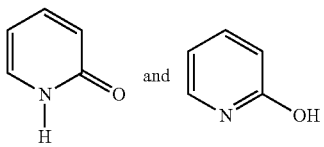 [SMILES: O=c1cccc[nH]1 ; Oc1ccccn1]

are considered equivalent in certain embodiments of this invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). If a Tricyclic Compound incorporates a double bond or a fused ring, both the cis- and trans-forms, as well as mixtures, are embraced within the scope of the invention. Also, for example, all keto-enol and imine-enamine forms of the compounds are included in the invention).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to apply equally to the salt, solvate, ester and prodrug of enantiomers, stereoisomers, rotamers, tautomers, positional isomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

Polymorphic forms of the Tricyclic Compounds, and of the salts, solvates, hydrates, esters and prodrugs of the Tricyclic Compounds, are intended to be included in the present invention.

Polymorphic forms of the Tricyclic Compounds, and of the salts, solvates, hydrates, esters and prodrugs of the Tricyclic Compounds, are intended to be included in the present invention.

The following abbreviations are used below and have the following meanings:
BINAP is racemic-2,2'-bis(diphenylphosphino)-1,1'-binaphthyl; BOC or Boc is tert-butyloxycarbonyl; CDI is carbonyl diimidazole; Ci/mmol is Curie/mmol; CSA is camphorsulfonic acid; DBPD is 2-(Di-t-butylphosphino)biphenyl, DBU is 1,8-diazabicyclo[5.4.0]undec-7-ene; DBN is 1,5-diazabicyclo[4.3.0]non-5-ene; DCC is dicyclohexylcarbodiimide; DCM is dichloromethane; Dibal-H is diisobutylaluminum hydride; DIPEA is N,N-Diisopropylethylamine; DMAP is dimethylaminopyridine; DME is dimethoxyethane; DMF is dimethylformamide; dppf is diphenylphosphinoferrocene; EDCI is 1-(3-dimethylaminopropyl)-3-ethylcarbodiimide; EtOAc is ethyl acetate; FABMS is fast atom bombardment mass spectrometry; HATU is O-(7-azabenzotriazol-1-yl)-N,N,N',N'-tetramethyluronium hexafluorophosphate; HOBT is 1-hydroxybenzotriazole; HOOBt is 3-hydroxy-1,2,3-benzotriazin-4 (3H)-one;
HPLC is high performance liquid chromatography; HRMS is high resolution mass spectrometry; Hunig's base is N,N-diisopropylethylamine;
LAH is lithium aluminum hydride; LDA is lithium diisopropylamide; LRMS is low resolution mass spectrometry; m-CPBA is m-chloroperbenzoic acid; MeOH is methanol; NaBH(OAc)$_3$ is sodium triacetoxyborohydride; NaBH$_4$ is sodium borohydride; NaBH$_3$CN is sodium cyanoborohydride; NaHMDS is sodium hexamethyldisilazane; NH$_4$OAc is ammonium acetate; p-TsOH is p-toluenesulfonic acid; p-TsCl is p-toluenesulfonyl chloride; Pd(PPh$_3$)$_4$ is tetrakis(triphenylphosphine)palladium (0); PPTS is pyridinium p-toluenesulfonate; PYBROP is bromotripyrrolidinophosphonium hexafluorophosphate; SEM is β-(trimethylsilyl)ethoxy]methyl; SEMCl is β-(trimethylsilyl)ethoxy]methyl chloride; TFA is trifluoroacetic acid; THF is tetrahydrofuran; TLC is thin-layer chromatography; TMAD is N,N,N',N'-tetramethylazodicarboxamide; Tr is triphenylmethyl; and Tris is tris(hydroxymethyl)aminomethane.

The Compounds of Formula (I)

The present invention provides Tricyclic Compounds of Formula (I):

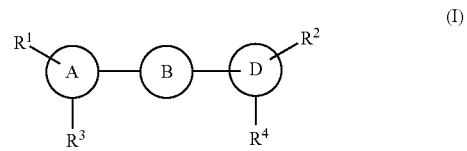

and pharmaceutically acceptable thereof, wherein A, B, D, $R^1$, $R^2$, $R^3$ and $R^4$ are defined above for the Compounds of Formula (I).

In one embodiment, B is selected from the group consisting of:

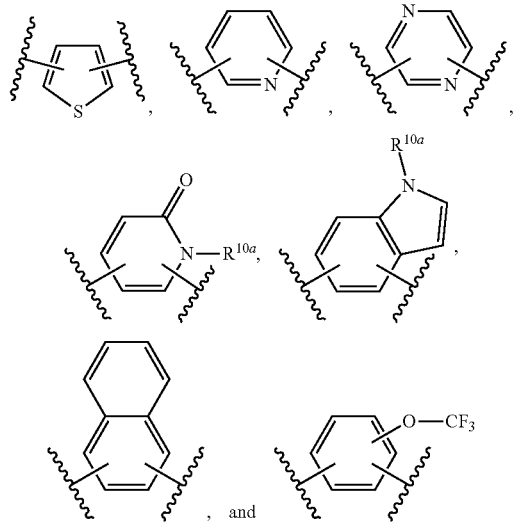

(wherein the truncated bonds indicate the point of attachment to A and D).

In another embodiment, A is

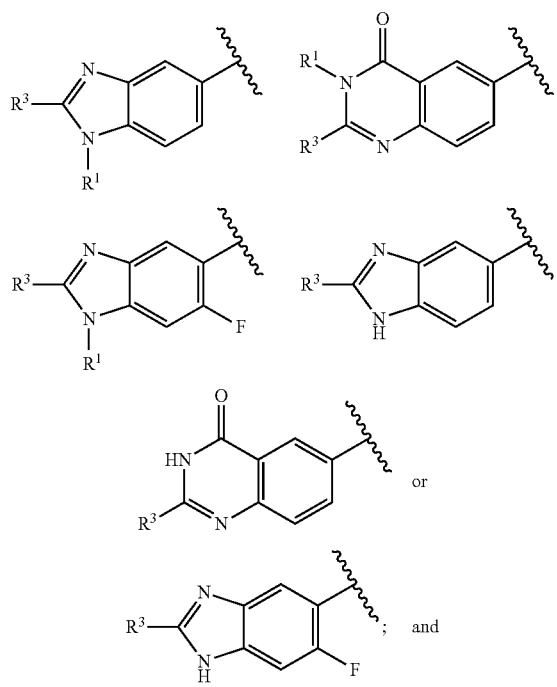

D is

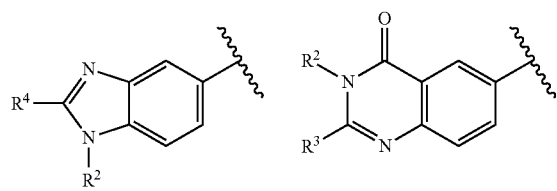

-continued

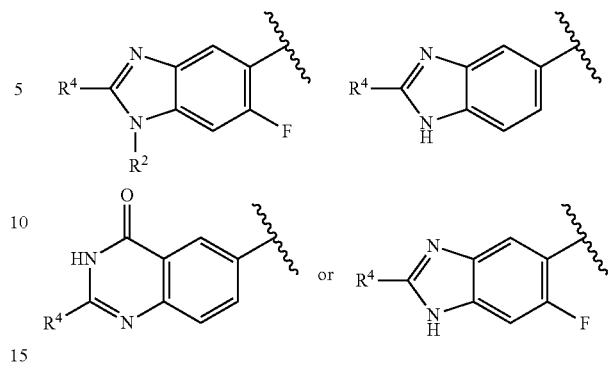

In still another embodiment, A and D are each independently selected from the group consisting of:

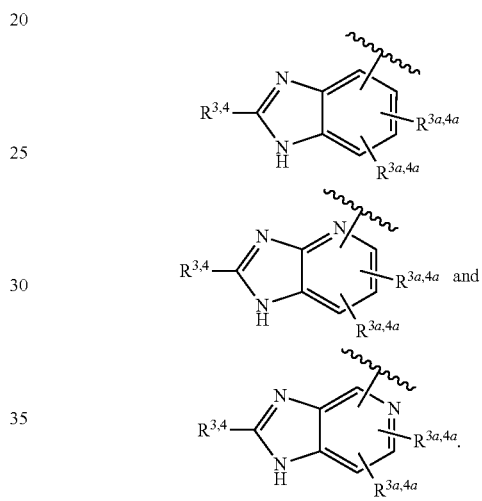

In yet embodiment, A and D are independently selected from the group consisting of:

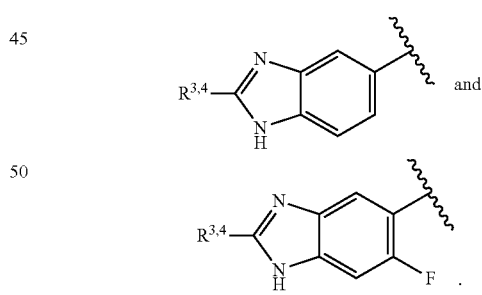

In one embodiment, $R^3$ and $R^4$ are independently selected from the group consisting of:

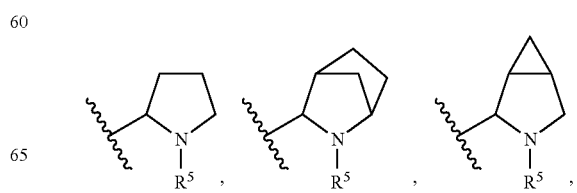

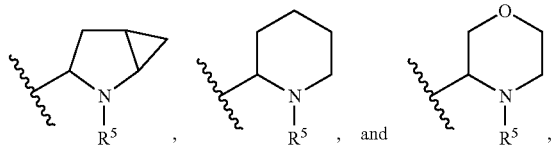

wherein $R^3$ and $R^4$ are optionally and independently substituted with one to two fluorine.

In another embodiment, $R^3$ and $R^4$ are independently selected from the group consisting of:

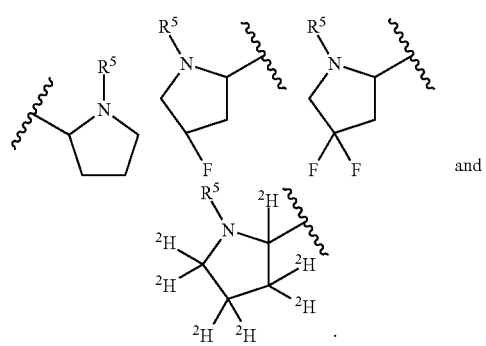

In one embodiment, A-$R^3$ and D-$R^4$ are each

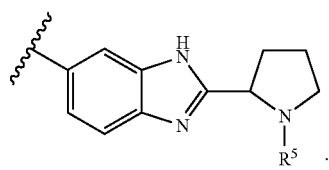

In one embodiment, each occurrence of $R^5$ is selected from the group consisting of:

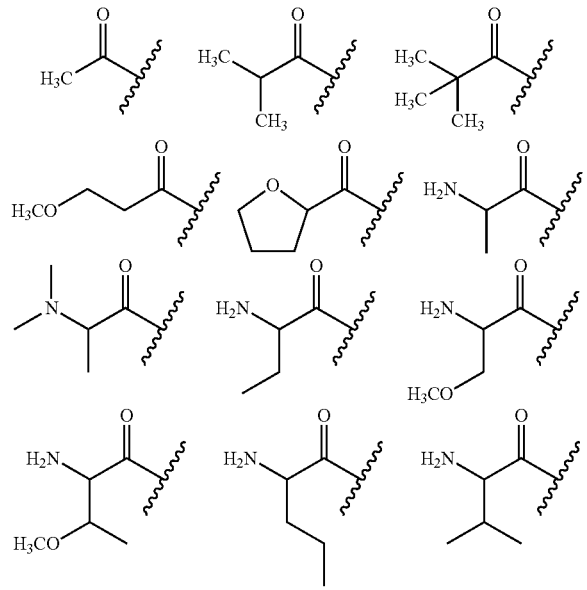

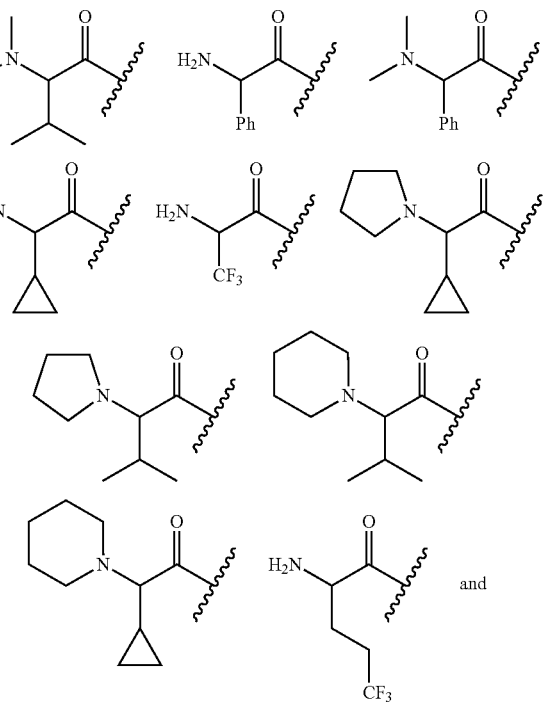

In another embodiment, each occurrence of $R^5$ is independently:

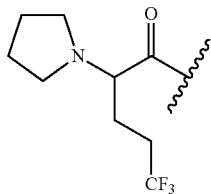

wherein $R^a$ is H, $C_1$-$C_4$ alkyl, $C_1$-$C_3$ fluoroalkyl, or phenyl, and $R^b$ is $C_1$-$C_3$ alkyl.

In yet another embodiment, each occurrence of $R^5$ is selected from the group consisting of:

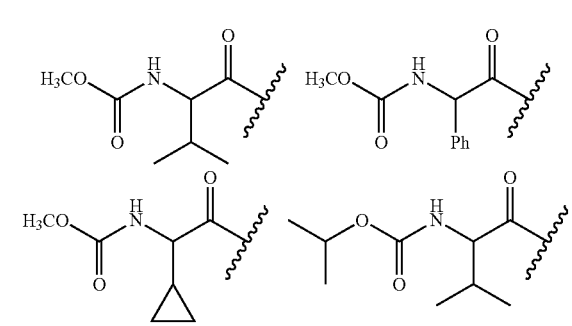

-continued

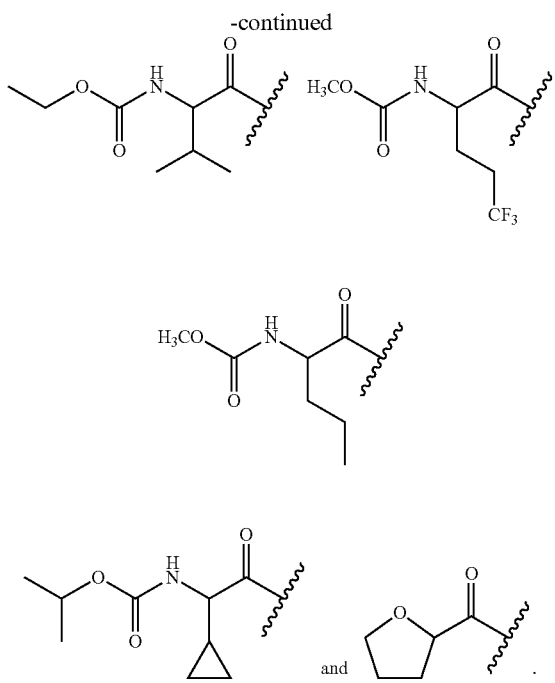

In still another embodiment, each occurrence of R⁵ is

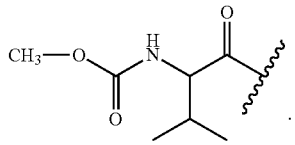 [SMILES: *C(=O)C(NC(=O)OC)C(C)C]

In another aspect, the invention relates to a compound of Formula (I), wherein

A is benzimidazolyl, wherein said benzimidazolyl is optionally substituted on a ring carbon atom with one to two fluoro;

B is a ring selected from the group consisting of:

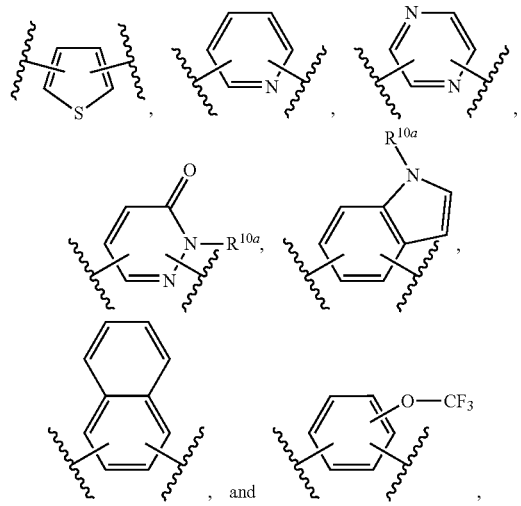

wherein B is optionally substituted on one or more ring carbon atoms by one to three $R^{10}$ and wherein when B is

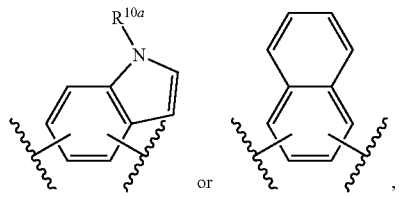

then A and D are each bonded to a common ring of B;

wherein $R^{10}$ is selected from the group consisting of H, $C_1$-$C_6$ alkyl and phenyl;

D is benzimidazolyl, wherein said benzimidazolyl is optionally substituted on a ring carbon atom with one to two fluoro;

$R^3$ and $R^4$ are independently selected from the group consisting of:

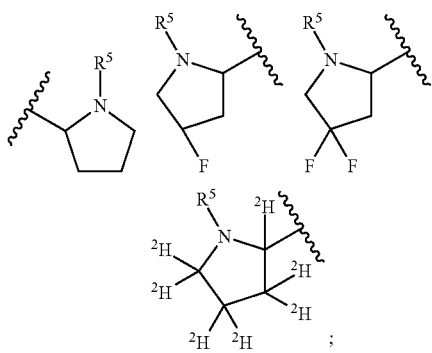

each occurrence of $R^5$ is independently selected from the group consisting of H and —C(O)—($C_1$-$C_6$ alkyl) optionally substituted by one to seven $R^{12}$ groups, wherein $R^{12}$ is selected from the group consisting of:

(i) —NHC(O)—O—($C_1$-$C_3$ alkyl)

(ii) $C_2$-$C_4$ alkynyl; and (iii) ²H; and $R^{10a}$ is H or $C_1$-$C_3$ alkyl.

In one embodiment of this aspect, A and D are independently selected from the group consisting of:

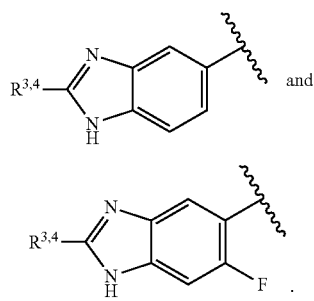

In another embodiment of this aspect, $R^3$ and $R^4$ are both
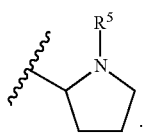
In yet another embodiment of this aspect, each occurrence of $R^5$ is
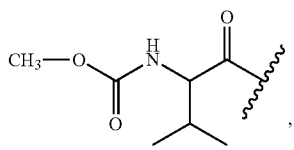
In another embodiment of this aspect, A-B-D forms the following substructure:
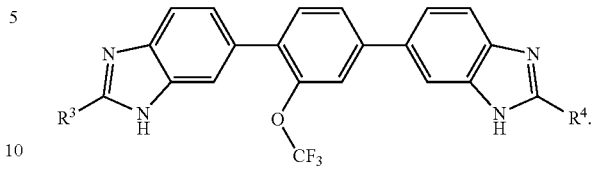
Non-limiting examples of the Compounds of Formula (I) include compounds 30, 31, 32, 33, 42, 43, 44, 55, 59, 64, 72, 91, 99, 103, 115, 117, 119, 121, 128, 129, 131, 132, 133, 134, and 135 as set forth below:
30
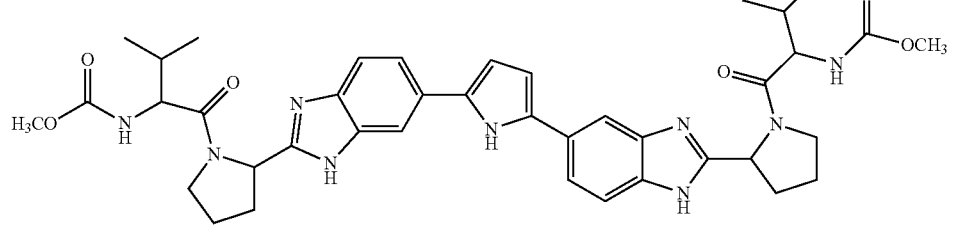
31
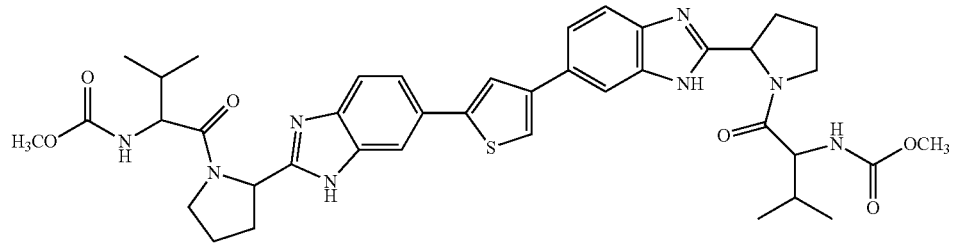
32
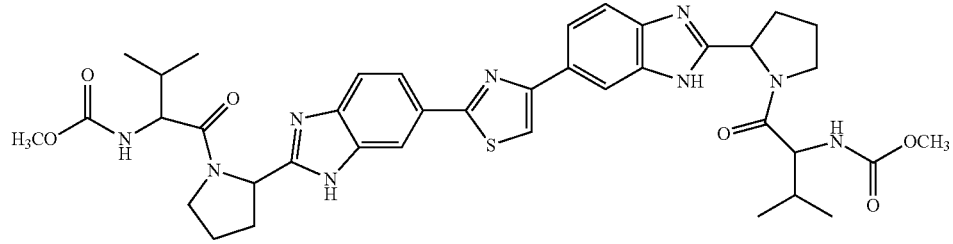
33
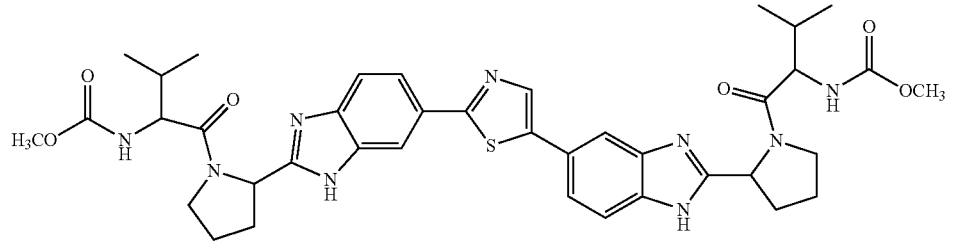

-continued
42
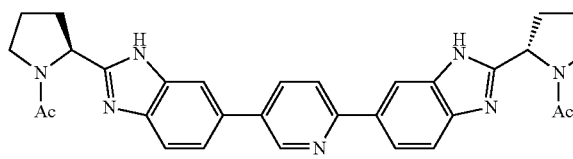
43
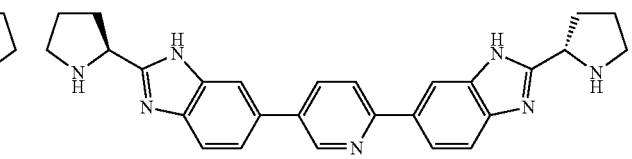
44
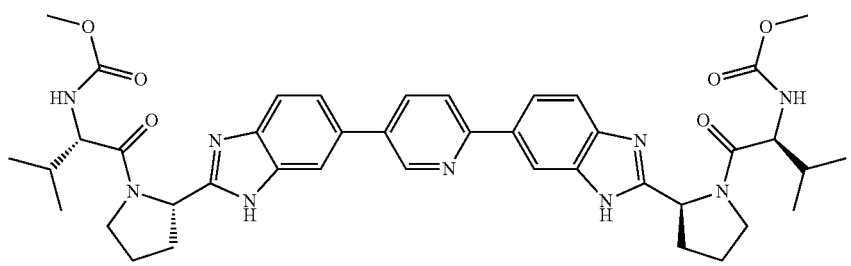
55
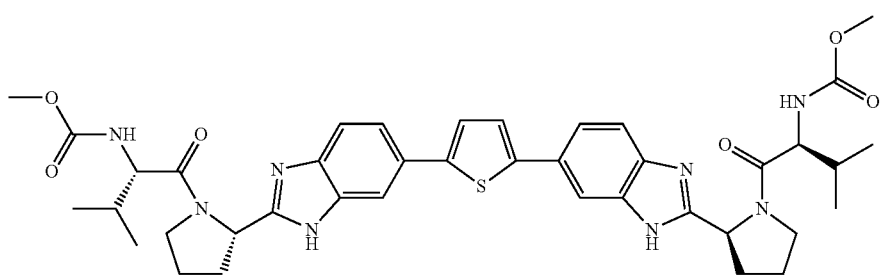
59
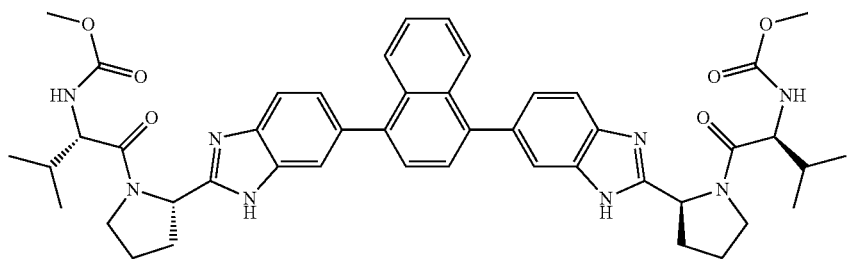
64
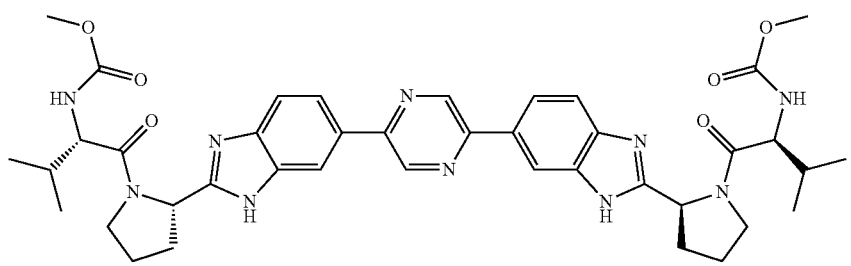
72
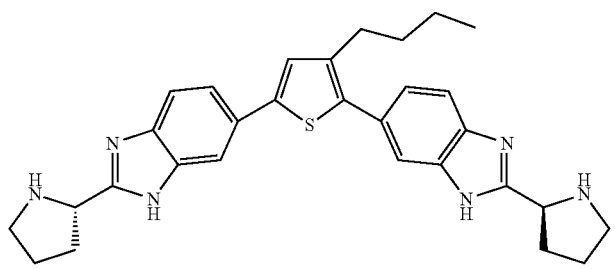

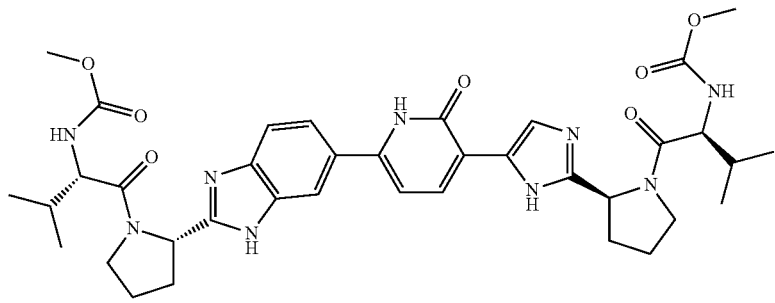
91
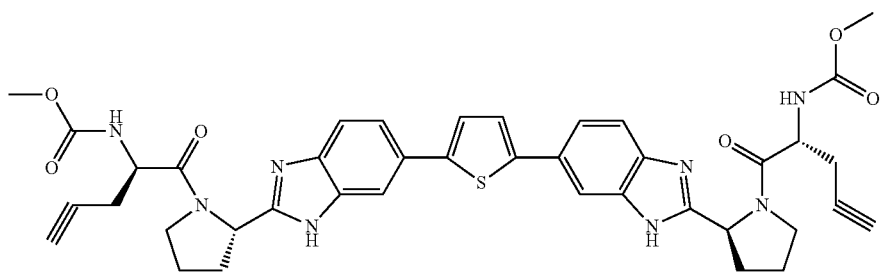
99
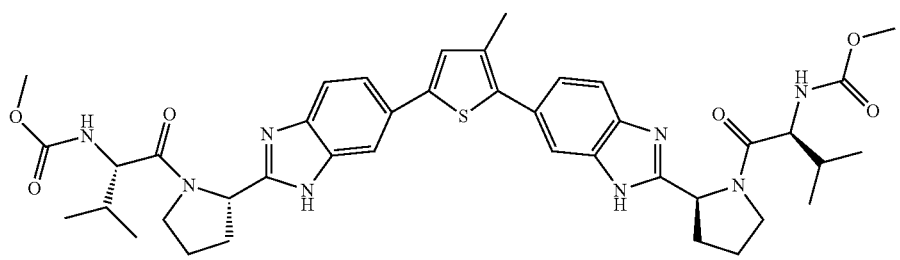
103
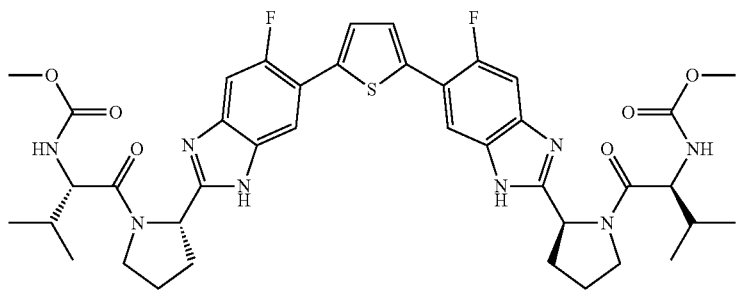
115
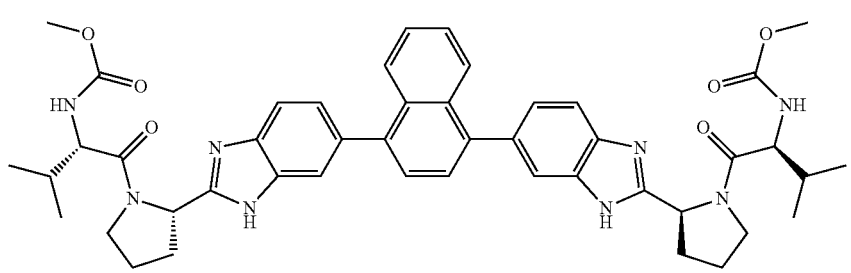
117

119
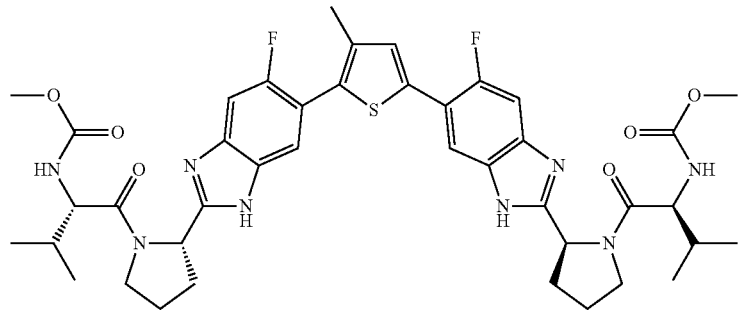
121
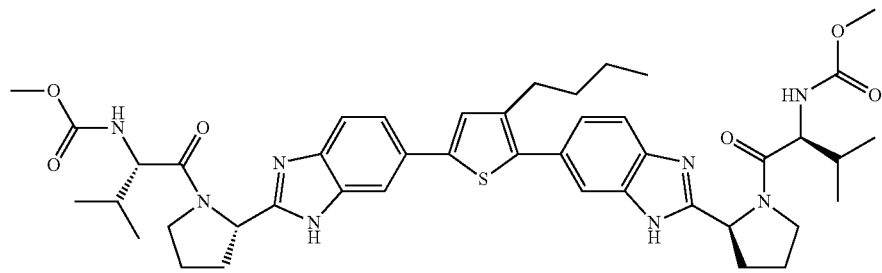
128
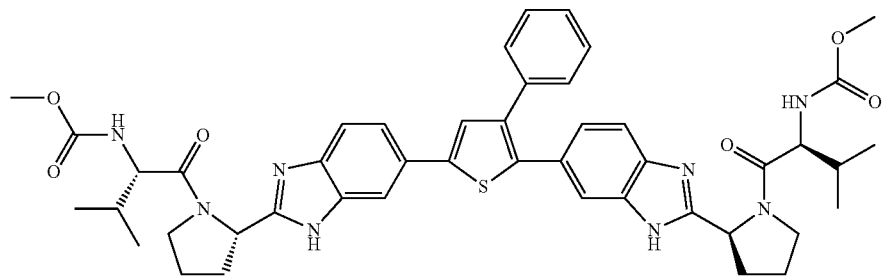
129
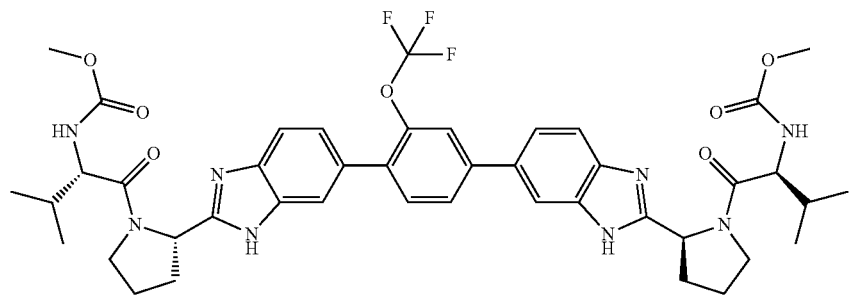
131
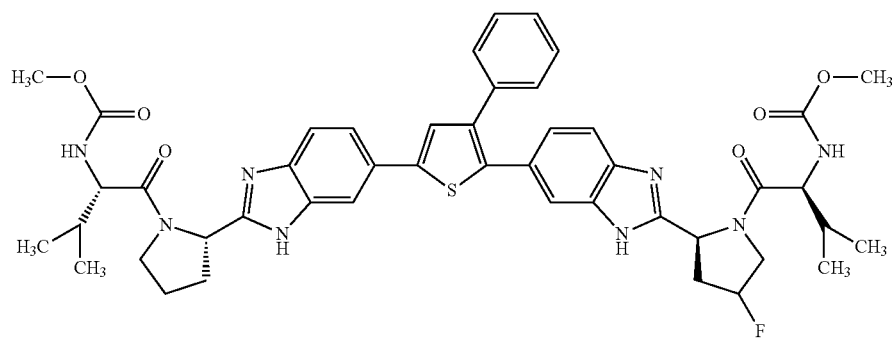

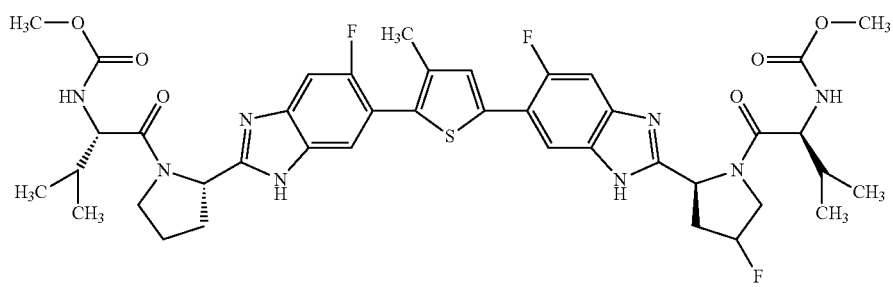

132

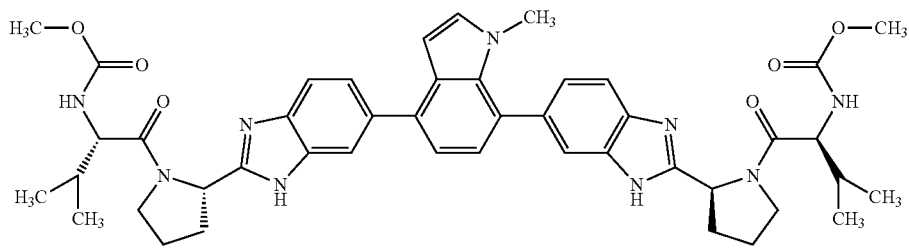

133

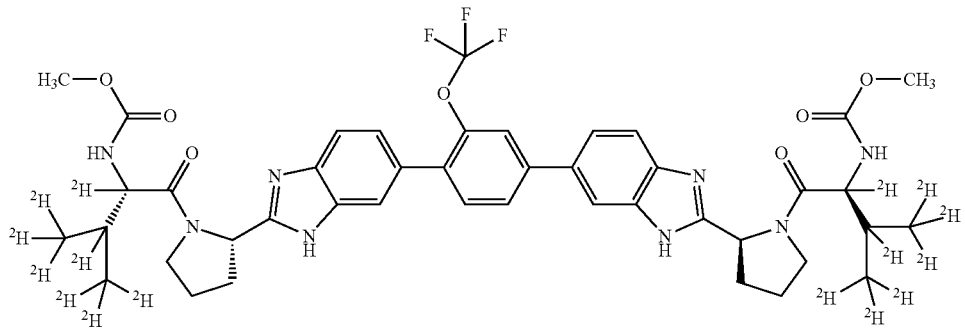

134

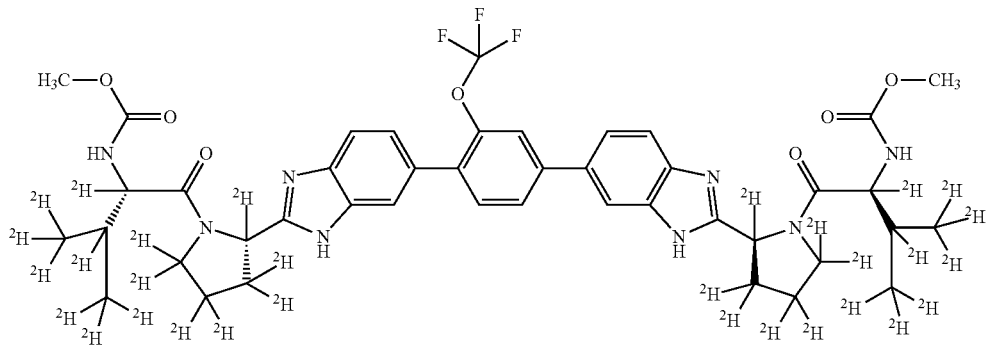

135 and pharmaceutically acceptable salts thereof.

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below and generalized in the schemes below. Alternative synthetic pathways and analogous structures will be apparent to those skilled in the art of organic synthesis. All stereoisomers and tautomeric forms of the compounds are contemplated.

The starting materials and reagents described in the Schemes below are either available from commercial suppliers such as Sigma-Aldrich (St. Louis, Mo.) and Acros Organics Co. (Fair Lawn, N.J.), or can be prepared using methods well-known to those of skill in the art of organic synthesis.

In some compounds contemplated, $R^3$ and/or $R^4$ contains a nitrogen atom, which can be synthesized through an amino acid derived intermediate, such as proline, 4-fluoroproline, 4,4-difluoroproline, (S)-2-piperidine carboxylic acid, valine, alanine, norvaline, etc. Methods have been described in the general literature as well as in Banchand U.S. Patent Publication No. 2009/0068140 (Published Mar. 9, 2009) for the preparation of such amino acid derivatives.

One skilled in the art of organic synthesis will recognize that the synthesis of the core of the Compounds of Formula (I) may require the need for the protection of certain functional groups (i.e., derivatization for the purpose of chemical compatibility with a particular reaction condition). Suitable protecting groups for the various functional groups of these compounds and methods for their installation and removal can be found in Greene et al., *Protective Groups in Organic Synthesis*, Wiley-Interscience, New York, (1999).

One skilled in the art of organic synthesis will also recognize that one route of the possible routes for the synthesis of the core of the Compounds of Formula (I) may be more desirable depending on the choice of appendage substituents. An example of such would be if the $R^5$ substituent is base sensitive and the cyclization method used to form Ring B is mediated by strong base. One skilled in the art of organic synthesis would plan a synthesis in which ring B is constructed before the appendage of the $R^5$ substituent.

Additionally, one skilled in the art will recognize that in some cases the order of reactions may differ from that presented herein to avoid functional group incompatibilities and amend the synthetic route accordingly. An example of such would be if the $R^1$ substituent is base sensitive and the $R^3$ is not-base sensitive and the method chosen for appended $R^3$ is mediated by a base. One skilled in the art of organic synthesis would plan a synthesis in which $R^3$ is attached to the core before the appendage of the $R^1$ substituent.

The preparation of the ring systems contemplated in this invention, have been described in the literature and in compendia such as "Comprehensive Heterocyclic Chemistry" editions I, II and III, published by Elsevier and edited by A. R. Katritzky & R. J. K. Taylor. One skilled in the art of organic chemistry will recognize that in some cases one or more of the rings of the contemplated invention can be constructed by cyclization methods or rearrangement reactions well known in the art of organic synthesis. Aromatic and heteroaromatic rings can be formed by cycloaddition reactions well known in the art which include the Diels-Alder, Hetero Diels-Alder and dipolar addition cycloaddition (e.g. 2+2 and 2+3) reactions. Heteroaromatic rings in many cases can be prepared via a cyclization reaction followed by removal of water such the intramolecular reaction of an aldehyde with an amine followed by loss of water. Cycloalkyl and heterocycloalkyl rings can be prepared by reduction of the related aromatic analog. Cycloalkyl and heterocycloalkyl rings can also be prepared by cyclization reaction. Examples of a cyclization reaction include the intermolecular reaction of an amine anion which a halide or the reaction with an amine with an aldehyde under reductive amination conditions such as conditions using sodium triacetoxyborohydride. Another such cyclization reaction is the intramolecular reaction of a hydroxyl anion with a halide. Oxygen containing heterocycloalkyl rings can be prepared by rearrangement reactions. One such rearrangement reaction is the Baeyer-Villiger rearrangement of a cyclic ketone to form lactones. These methods are well in the art of organic chemistry and have been described in the literature and in compendia such as "Comprehensive Heterocyclic Chemistry" editions I, II and III, published by Elsevier and edited by A. R. Katritzky & R. J. K. Taylor to prepare the ring systems contemplated in this invention.

The functionalization of the ring systems contemplated in this invention, have been described in the literature and in compendia such as "Comprehensive Heterocyclic Chemistry" editions I, II and III, published by Elsevier and edited by A. R. Katritzky & R. J. K Taylor. One skilled in the art of organic chemistry will recognize that the use of a functionalized pre-formed ring such as X-A, can be coupled with a X'—B or X'—B-D wherein, X and X' are suitable functional groups that can undergo cross-coupling reactions and rings A, B, and D are as described above. One such set of suitable functional groups which can participate in transition metal-mediated coupling chemistry are —B(OH)$_2$, —B(Oalkyl)$_2$, —B(N-methyliminodiacetic acid), Sn(alkyl)$_3$, —MgBr, —MgCl, —ZnBr, —ZnCl. Another set of suitable functional groups which participate in transition metal-mediated coupling chemistry are Cl, Br, I and O-triflate. The recent discovery and use of N-methyliminodiacetic acid boronates has been described by M. Burke et al. in *J. Am. Chem. Soc.* 2009 web edition 10.1021/ja901416p. Suitable cross-coupling methods include, but are not limited to, a Stille coupling (see Choshi et al., *J. Org. Chem.*, 62:2535-2543 (1997), and Scott et al., *J. Am. Chem. Soc.*, 106:4630 (1984)), a Suzuki-Miayura coupling (*Angew Chem. Int. Ed. Engl* 2001, 40, 4544), a Negishi coupling (see Zhou et al., *J. Am. Chem. Soc.*, 127: 12537-12530 (2003)), and a Kumada coupling (see Kumada, *Pure Appl. Chem.*, 52:669 (1980) and Fu et al., *Angew. Chem.* 114:4363 (2002) where one coupling partner is chosen from each of the above sets.

Manipulation of the required substitution patterns have also been described in the available chemical literature as summarized in compendia such as "Comprehensive Organic Chemistry" published by Elsevier and edited by D. H. R. Barton and W. D. Ollis; "Comprehensive Organic Functional Group Transformations" edited by A. R. Katritzky & R. J. K. Taylor and "Comprehensive Organic Transformation" published by Wily-CVH and edited by R. C. Larock and "March's Advanced Organic Chemistry: Reactions, Mechanism and Structure" by M. Smith and J. March, $6^{th}$ Edition and published by Wiley-Interscience, 2007.

One skilled in the art of organic synthesis will recognize that the synthesis of certain compounds of Formula (I) require the construction of an amide bond. Methods useful for making such amide bonds, include but are not limited to, the use of a reactive carboxy derivative (e.g., acid halide, or ester at elevated temperatures) or the use of an acid with a coupling reagent (e.g., EDCI, DCC, HATU, PyBrop) with an amine.

One skilled in the art of organic synthesis will recognize that the synthesis of certain compounds of Formula (I) require a carbon-nitrogen or carbon-oxygen bond. One method for the construction of a carbon-oxygen bond includes the reaction of the oxygen atom present in such functional groups as a carboxylic acid or an alcohol with a compound containing a carbon atom functionalized with a leaving group in the presence of a base such as cesium carbonate or LDA. One method for the construction of a carbon-nitrogen bond includes the reaction of the amine atom present in such functional groups as an amide or an amine with a compound containing a carbon atom functionalized with a leaving group in the presence of a base such as cesium carbonate or LDA. Typical leaving groups include but are not limited to a halide or O-mesylate.

The starting materials used and the intermediates prepared using the methods set forth in the Schemes below may be isolated and purified if desired using conventional techniques, including but not limited to filtration, distillation, crystallization, chromatography and the like. Such materials can be characterized using conventional means, including physical constants and spectral data.

EXAMPLES

General Methods

Solvents, reagents, and intermediates that are commercially available were used as received. Reagents and intermediates that are not commercially available were prepared in the manner as described below. $^1$H NMR spectra were obtained on a Bruker Avance 500 (500 MHz) and are reported as ppm down field from Me$_4$Si with number of protons, multiplicities, and coupling constants in Hertz indicated parenthetically. Where LC/MS data are presented, analyses were performed using an Applied Biosystems API-100 mass spectrometer and Shimadzu SCL-10A LC column: Altech platinum C18, 3 micron, 33 mm×7 mm ID; gradient flow: 0 minutes—10% CH$_3$CN, 5 minutes—95% CH$_3$CN, 5-7 minutes—95% CH$_3$CN, 7 minutes—stop. The retention time and observed parent ion are given. Flash column chromatography was performed using pre-packed normal phase silica from Biotage, Inc. or bulk silica from Fisher Scientific. Unless otherwise indicated, column chromatography was performed using a gradient elution of hexanes/ethyl acetate, from 100% hexanes to 100% ethyl acetate.

Example 1

Preparation of Intermediate Compound Int-1a

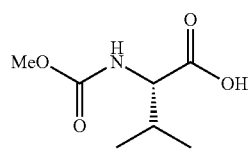

Int-1a

To a solution of L-valine (10.0 g, 85.3 mmol) in 1 M aqueous NaOH solution (86 mL) at room temperature was added solid sodium carbonate (4.60 g, 43.4 mmol). The solution was cooled to 0° C. (ice bath) and to the cooled solution was added methyl chloroformate (7.20 mL, 93.6 mmol) dropwise over 20 minutes. The reaction mixture was then allowed to warm to room temperature on its own and stirred at room temperature for an additional 4 hours. The reaction mixture was then diluted with diethyl ether (100 mL), the resulting solution was cooled to at 0° C., and concentrated hydrochloric acid (18 mL, 216 mmol) was added. The resulting solution was extracted with EtOAc (3×100 mL) and the combined organics were dried over MgSO$_4$, filtered and concentrated in vacuo to provide compound Int-1a (13.5 g, 90%), which was used without further purification.

Example 2

Preparation of Intermediate Compound Int-2a

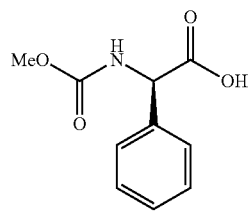

Int-2a

To a solution of D-phenylglycine (10.0 g, 66.1 mmol) and NaOH (21.2 g, 265 mmol) in water (60 mL) at 0° C. was added methyl chloroformate (10.2 mL, 133 mmol) dropwise over 20 minutes. The resulting reaction was allowed to stir at 0° C. for 1 hour, and then was acidified using concentrated hydrochloric acid (25 mL, 300 mmol). The acidic solution was extracted with EtOAc (3×100 mL) and the combined organics were dried over MgSO$_4$, filtered and concentrated in vacuo to provide compound Int-2a (12.6 g, 91%), which was used without further purification.

The following intermediates can be prepared by the reaction of L-Alanine and 4-F phenylglycine respectively with methyl chloroformate (Aldrich Inc.) as above

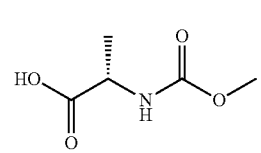

Int-2b

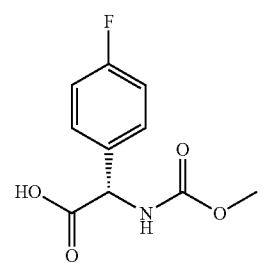

Int-2c

Example 3

Preparation of Intermediate Compound Int-3a

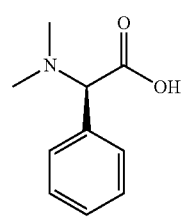

Int-3a

A solution of D-phenylglycine (20.0 g, 132 mmol), 37% aqueous formaldehyde (66 mL, 814 mmol) and 5% Pd on carbon (8.0 g, mmol) in a mixture of methanol (80 mL) and 1 N HCl (60 mL) was placed on a hydrogenation shaker and shook at 35-40 psi hydrogen for 4 hours. It was then filtered through a celite pad and concentrated in vacuo to provide compound Int-3a (29.7 g, quant.) as a white solid, which was used without further purification.

Example 4

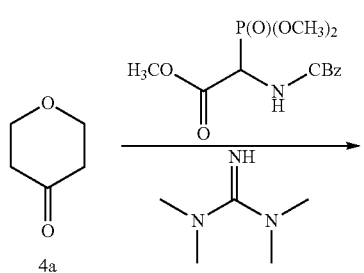

4a

-continued

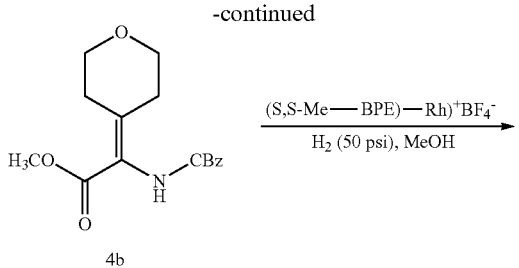
4b

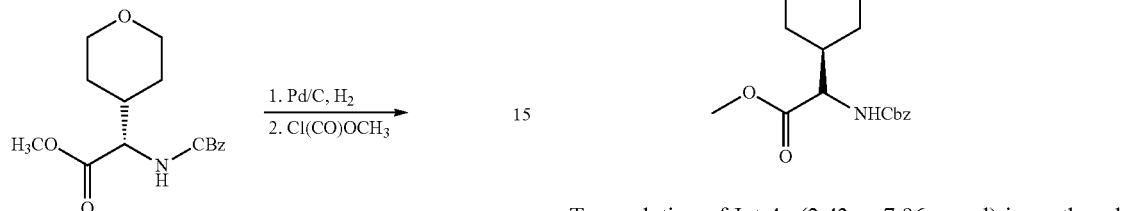
4c

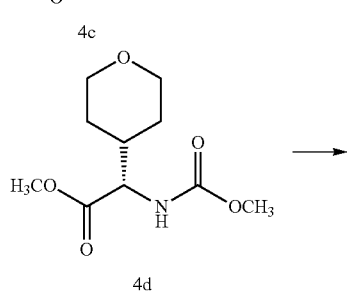
4d

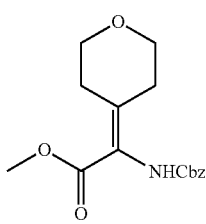
4e

Step A—Preparation of Compound Int-4a

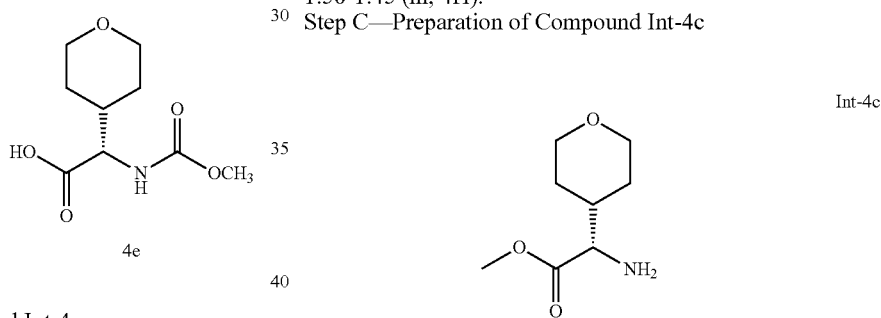

To a solution of methyl 2-(benzyloxycarbonylamino)-2-(dimethoxyphosphoryl)acetate (10.0 g, 30.2 mmol) (Prep of Wittig: Hamada, Makoto; Shinada, Tetsuro; Ohfune, Yasufumi; ORLEF7; Organic Letters; English; 11; 20; 2009; 4664-4667) in THF (100 mL) at −20° C. was added tetramethylguanidine (4.20 mL, 33.2 mmol). The reaction mixture was stirred at −20° C. for 1 h then dihydro-2H-pyran-4(3H)-one (4a) was added (3.1 mL, 33.2 mmol) in THF (5 mL) and the reaction mixture was warmed to rt and stirred overnight. EtOAc (200 mL) was added and the organic mixture was washed with water (3×50 mL) and brine (50 mL). The organic layers were combined and dried with Na₂SO₄, filtered and concentrated. The crude product was purified by flash chromatography on an ISCO 330 g Redi-Sep column using 0-35% EtOAc/hexanes as the eluent to yield the desired product Int-4a as a white solid (615 mg, 45%). $^1$H NMR (CDCl₃) δ 7.40-7.30 (m, 5H), 6.00 (br s, 1H), 5.12 (s, 2H), 3.80-3.65 (m, 7H), 2.92 (m, 2H), 2.52-2.48 (m, 2H).

Step B—Preparation of Compound Int-4b

Int-4b

To a solution of Int-4a (2.43 g, 7.96 mmol) in methanol (160 mL) previously purged with N₂ was added (−)-1,2-Bis((2S,5S)-2,5-dimethylphospholano)ethane (cyclooctadiene) rhodium (I) tetrafluoroborate (CAS #213343-65-8) (487 mg, 0.880 mmol) under N₂. The mixture was shaken in a Parr shaker apparatus for 18 h at 50 psi of H₂. After evacuating the hydrogen, the suspension was filtered and the filtrate was concentrated to yield the desired product Int-4b as a white solid (1.30 g, 53%). $^1$H NMR (CDCl₃) δ 7.40-7.30 (m, 5H), 5.32 (br s, 1H), 5.12 (s, 2H), 4.40-4.30 (m, 1H), 4.00-3.95 (m, 2H), 3.75 (s, 3H), 3.40-3.25 (m, 2H), 2.10-1.95 (m, 1H), 1.50-1.45 (m, 4H).

Step C—Preparation of Compound Int-4c

Int-4c

To a suspension of 50% palladium on carbon (10% wet, 200 mg) in absolute ethanol (20 mL) under nitrogen was added Int-4b (1.06 g, 3.45 mmol). With stirring, the solution was placed under vacuum for 30 seconds and then was opened to a hydrogen gas balloon for 2 h. After evacuating the hydrogen, the suspension was filtered through a Celite pad and the pad washed with ethanol (2×20 mL). The filtrate was concentrated to yield the desired product Int-4c as a colorless oil (585 mg, 98%). $^1$H NMR (CDCl₃) δ 4.06-3.96 (m, 2H), 3.73 (s, 3H), 3.48-3.28 (m, 3H), 1.92-1.78 (m, 1H), 1.61-1.47 (m, 6H).

Step D—Preparation of Compound Int-4d

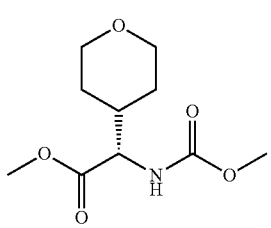
Int-4d

To the solution of compound Int-4c (585 mg, 3.37 mmol) and triethylamine (0.710 mL, 5.09 mmol) in CH$_2$Cl$_2$ (6 mL) was added methyl chloroformate (0.290 mL, 3.76 mmol). The reaction mixture was stirred at rt overnight. Water (15 mL) was added and the aqueous mixture was extracted with CH$_2$Cl$_2$ (3×20 mL). The combined organic layers were dried over Na$_2$SO$_4$, filtered and concentrated. The crude product was purified by flash chromatography on an ISCO 24 g Redi-Sep column using 0-3% MeOH/CH$_2$Cl$_2$ as the eluent to yield the desired product Int-4d as a colorless oil (600 mg, 77%). $^1$H NMR (CDCl$_3$) δ 5.27-5.18 (m, 1H), 4.38-4.28 (m, 1H), 4.06-3.96 (m, 2H), 3.75 (s, 3H), 3.69 (s, 3H), 3.39-3.30 (m, 2H), 2.09-1.94 (m, 1H), 1.59-1.48 (m, 4H).

Step E—Preparation of Compound Int-4e

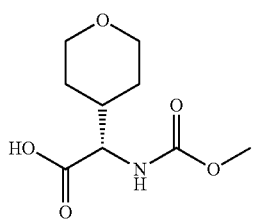

Int-4e

To the solution of compound Int-4d (600 mg, 2.59 mmol) in THF (5 mL) was added lithium hydroxide monohydrate (218 mg, 5.19 mmol) in water (5 mL). The reaction mixture was stirred at rt for 2 h then concentrated to half volume. The aqueous mixture was then acidified with 6N HCl and extracted with EtOAc (7×50 mL). The combined organic layers were dried over Na$_2$SO$_4$, filtered and concentrated to yield the desired product Int-4e as an off-white solid (485 mg, 86%). $^1$H NMR (CD$_3$OD) δ 4.09-4.07 (m, 1H), 3.96-3.92 (m, 2H), 3.65 (s, 3H), 3.40-3.34 (m, 2H), 2.10-1.99 (m, 1H), 1.56-1.47 (m, 4H).

Example 5

Preparation of Compound Int-5f

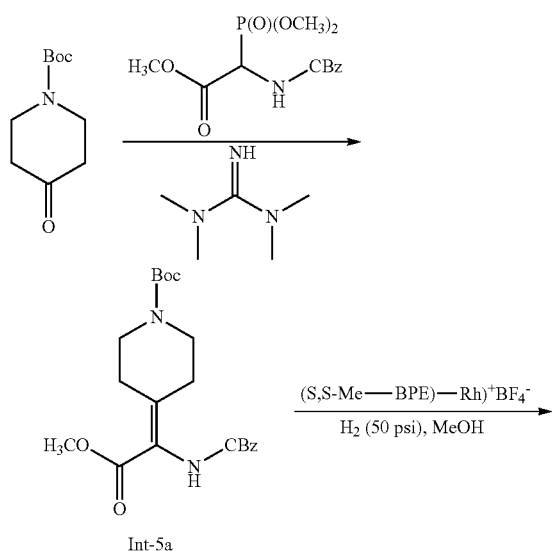

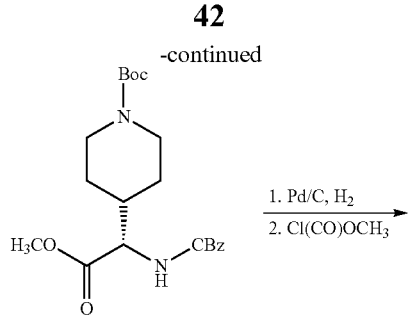

Int-5b

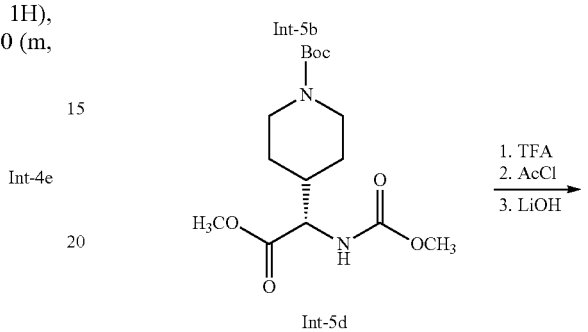

Int-5d

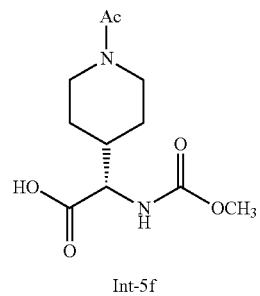

Int-5f

Step A—Preparation of Compound Int-5a

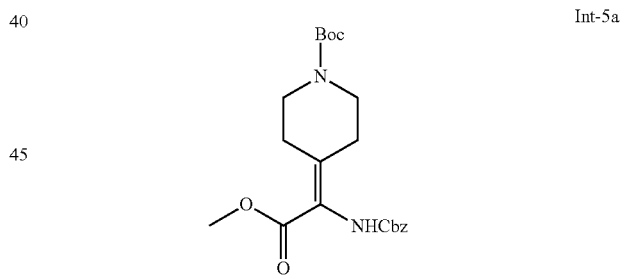

Int-5a

To a solution of methyl 2-(benzyloxycarbonylamino)-2-(dimethoxyphosphoryl)acetate (1.50 g, 4.52 mmol) in THF (5 mL) at −20° C. was added tetramethylguanidine (625 μL, 4.98 mmol). The reaction mixture was stirred at −20° C. for 1 h then tert-butyl 4-oxopiperidine-1-carboxylate was added (992 mg, 4.97 mmol) in THF (2 mL) and the reaction mixture was warmed to rt and stirred overnight. EtOAc (90 mL) was added and the organic mixture was washed with water (3×20 mL) and brine (25 mL). The combined organic layers were dried over Na$_2$SO$_4$, filtered and concentrated. The crude product was purified by flash chromatography on an ISCO 40 g Redi-Sep column using 0-35% EtOAc/hexanes as the eluent to yield the desired product Int-5a as a white semi-solid (1.1 g, 61%). $^1$H NMR (CDCl$_3$) δ 7.40-7.30 (m, 5H), 6.02 (br s, 1H), 5.12 (s, 2H), 3.80-3.40 (m, 7H), 2.90-2.80 (m, 2H), 2.45-2.35 (m, 2H), 1.45 (s, 9H).

Step B—Preparation of Compound Int-5b

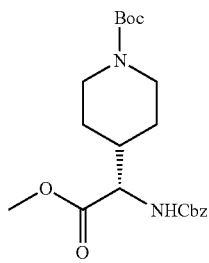

To a solution of Int-5a (1.30 g, 3.21 mmol) in methanol (90 mL) previously purged with N₂ was added (−)-1,2-Bis((2S,5S)-2,5-dimethylphospholano)ethane (cyclooctadiene) rhodium (I) tetrafluoroborate (CAS#213343-65-8) (197 mg, 0.354 mmol) under N₂. The mixture was shaken in a Parr shaker apparatus for 18 h at 50 psi of H₂. After evacuating the hydrogen, the suspension was filtered and the filtrate was concentrated to yield the desired product Int-5b as a colorless oil (1.00 g, 77%). ¹H NMR (CDCl₃) δ 7.40-7.30 (m, 5H), 5.35-5.25 (m, 1H), 5.10 (s, 2H), 4.40-4.35 (m, 1H), 4.20-4.10 (m, 2H), 3.70 (s, 3H), 2.70-2.55 (m, 2H), 2.00-1.90 (m, 1H), 1.65-1.40 (m, 11H), 1.30-1.20 (m, 2H).

Step C—Preparation of Compound Int-5c

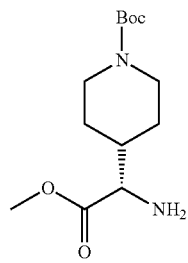

To a solution of 50% palladium on carbon (10% wet, 250 mg) in absolute ethanol (20 mL) under nitrogen was added Int-5b (1.00 g, 2.46 mmol). With stirring, the solution was placed under vacuum for 30 seconds and then was opened to a hydrogen gas balloon for 2 h. After evacuating the hydrogen, the suspension was filtered through a Celite pad and the pad washed with ethanol (2×20 mL). The filtrate was concentrated to yield the desired product Int-5c as a colorless oil (670 mg, quant.). ¹H NMR (CDCl₃) δ 4.21-4.08 (m, 2H), 3.73 (s, 3H), 3.31 (d, J=6.0 Hz, 1H), 2.75-2.57 (m, 2H), 1.84-1.70 (m, 1H), 1.68-1.56 (m, 1H), 1.45 (s, 9H), 1.45-1.20 (m, 5H).

Step D—Preparation of Compound Int-5d

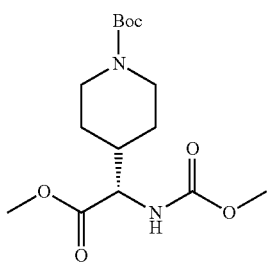

To the solution of compound Int-5c (670 mg, 2.46 mmol) and triethylamine (0.520 mL, 3.73 mmol) in CH₂Cl₂ (10 mL) was added methyl chloroformate (0.210 mL, 2.72 mmol). The reaction mixture was stirred at rt overnight. Water (20 mL) was added and the aqueous mixture was extracted with CH₂Cl₂ (2×15 mL). The combined organic layers were dried over Na₂SO₄, filtered and concentrated. The crude product was purified by flash chromatography on an ISCO 24 g Redi-Sep column using 0-3% MeOH/CH₂Cl₂ as the eluent to yield the desired product Int-5d as an off-white solid (515 mg, 63%). ¹H NMR (CDCl₃) δ 5.26-5.17 (m, 1H), 4.38-4.30 (m, 1H), 4.20-4.07 (m, 2H), 3.75 (s, 3H), 3.68 (s, 3H), 2.71-2.57 (m, 2H), 2.00-1.85 (m, 1H), 1.87-1.48 (m, 2H), 1.44 (s, 9H), 1.35-1.18 (m, 2H).

Step E—Preparation of Compound Int-5e

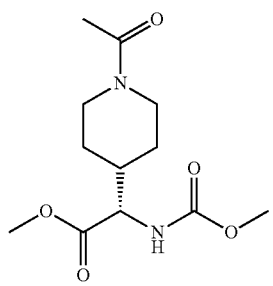

Compound Int-5d (300 mg, 0.908 mmol) was dissolved in a mixture of TFA (2 mL) and CH₂Cl₂ (10 mL) and the solution was stirred at rt for 1 h before it was concentrated in vacuo to give a solid. To this residue triethylamine (0.760 mL, 5.45 mmol) in CH₂Cl₂ (10 mL) was added followed by acetic anhydride (0.086 mL, 0.915 mmol). The reaction mixture was stirred at rt overnight then concentrated. The crude product was purified by flash chromatography on an ISCO 12 g Redi-Sep column using 0-4% MeOH/CH₂Cl₂ as the eluent to yield the desired product Int-5e as a colorless oil (247 mg, 99%). ¹H NMR (CDCl₃) δ 5.27-5.21 (m, 1H), 4.73-4.62 (m, 1H), 4.42-4.32 (m, 1H), 3.69 (s, 3H), 3.18 (s, 3H), 3.18-3.09 (m, 1H), 3.07-2.95 (m, 1H), 2.55-2.41 (m, 1H), 2.07 (s, 3H), 1.78-1.49 (m, 3H), 1.38-1.21 (m, 2H).

Step F—Preparation of Compound Int-5f

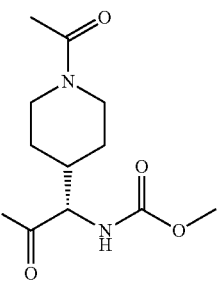

To the solution of compound Int-5e (247 mg, 2.59 mmol) in THF (3 mL) was added lithium hydroxide monohydrate (77 mg, 1.83 mmol) in water (3 mL). The reaction mixture was stirred at rt overnight then concentrated to half volume. The aqueous mixture was then acidified with 1N HCl to pH 4 and extracted with EtOAc (7×15 mL). The combined organics were dried over Na₂SO₄, filtered and concentrated to yield the desired product Int-5f as an off-white solid (106 mg, 45%). ¹H NMR (CD₃OD) δ 5.52-5.43 (m, 1H), 4.71-4.62 (m, 1H), 4.44-4.31 (m, 1H), 3.91-3.81 (M, 1H), 3.70 (s, 3H), 3.12-2.99 (m, 1H), 2.58-2.46 (m, 1H), 2.10 (m, 4H), 1.86-1.54 (m, 2H), 1.50-1.21 (m, 3H).

Example 6

Preparation of Intermediate Compound Int-6c

Step A—Synthesis of Compound Int-6b

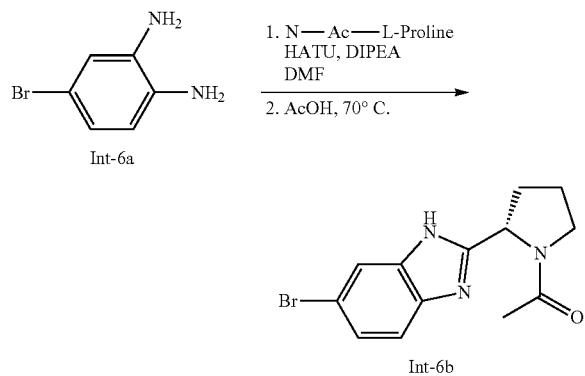

To a solution of compound Int-6a (6.1 g, 32.7 mmol), N-acetyl-L-proline (5.4 g, 34.35 mmol) and HATU (13.7 g, 34.35 mmol) in anhydrous DMF (100 mL) was added DIPEA (Hunigs base) (16.91 mL, 96.9 mmol) dropwise over 15 minutes at ice temperature. The reaction was warmed to room temperature and stirred for 3 hours. The reaction was then diluted with EtOAc (500 mL) and the organic layer washed with water (200 mL×2). The aqueous layer was back-extracted with EtOAc (100 mL×2).

The combined organic layers were washed with brine, dried over MgSO₄, filtered and concentrated. The crude product was purified using flash chromatography using a 1%-2% MeOH/CH₂Cl₂ as eluent to provide the intermediate amide (4.1 g). The amide was dissolved in glacial acetic acid and was heated at 60-70° C. for 1 hour. The reaction mixture was diluted with EtOAc (100 mL) and cooled in an ice bath. Saturated Na₂CO₃ solution was added slowly until the pH=8. The organic layer was separated and the aqueous layer was extracted with EtOAc (250 mL×2). The combined organic layers were washed with water and brine, dried over MgSO₄, filtered and concentrated in vacuo to provide compound Int-6b (3.75 g, 38%). MS: MH⁺=308.

Step B—Synthesis of Compound Int-6c

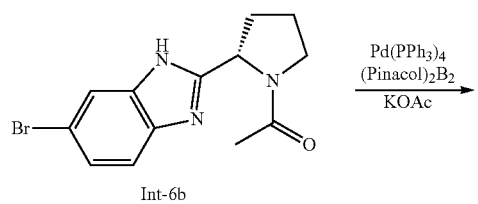

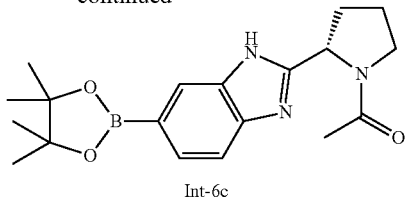

Compound Int-6b (925 mg, 3 mmol), (Pinacol)₂B₂ (1.6 g, 6.3 mmol), Pd(PPh₃)₄ (174 mg, 0.15 mmol), potassium acetate (736 mg, 7.5 mmol) and 1,4-dioxane (100 mL) were added to a 350 mL pressure vessel. The resulting mixture was degassed, purged with nitrogen and stirred at 80° C. for 17 hours. After the reaction was cooled to room temperature the solution was diluted with CH₂Cl₂ (300 mL) and filtered through a celite plug. The filtrate was washed with NaHCO₃ solution (50 mL) and water (50 mL). The combined organic layers were washed with brine, dried over MgSO₄, filtered and concentrated. The crude product was purified using flash chromatography using a 0-5% MeOH/CH₂Cl₂ as eluent to provide compound Int-6c (750 mg, 70%, contains some pinacol). MS: MH⁺=356.2; ¹H NMR (500 MHz, CD₃OD): δ 8.1-7.4 (m, 3H), 5.3 (m, 1H), 3.9 (m, 1H), 3.7 (m, 1H), 2.4 (m, 1H), 2.0-2.2 (m, 6H), 1.39 (bs, 12H).

Example 7

Preparation of Compounds 42 and Int-7a

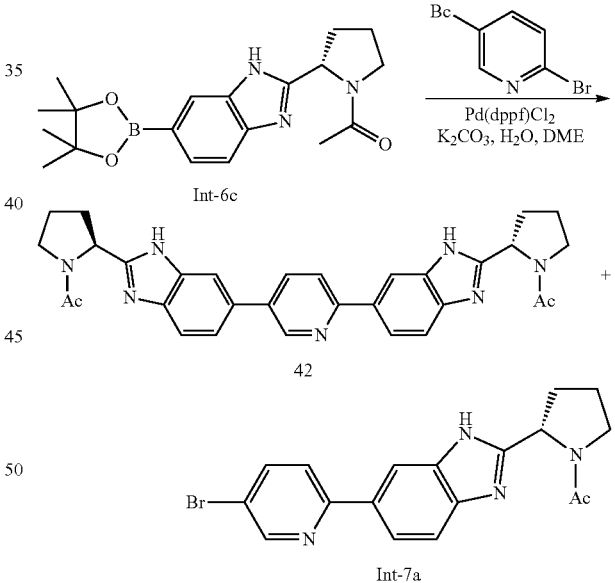

A round bottomed flask was charged with compound Int-6c (300 mg, 0.84 mmol), 2,5-dibromopyridine (100 mg, 0.042 mmol), Pd(dppf)Cl₂ (34 mg, 0.042 mmol), potassium carbonate (290 mg, 2.1 mmol), 5 mL DME and water. The reaction was heated to about 90° C. and allowed to stir at this temperature for 20 hours. The reaction mixture was cooled to room temperature, diluted with EtOAc (100 mL) and filtered through a celite pad. The filtrate was concentrated in vacuo and the resulting residue was purified using reverse phase HPLC using Acetonitrile/H₂O eluent to provide compound 42 (42 mg). MS: MH⁺=534.3. ¹H NMR (500 MHz, CD₃OD): δ 9.06 (m, 1H), 8.49 (m, 1H), 8.34 (m, 2H), 8.19 (m, 1H), 8.1

(m, 1H), 7.89-8.00 (m, 3H), 5.43 (m, 2H), 3.94 (m, 2H), 3.82 (m, 2H), 2.64 (m, 2H), 2.20-2.32 (m, 12H).

Compound Int-7a (46 mg) was also collected as a side product. MS: M⁺=385.2. ¹H NMR (500 MHz, CD₃OD): δ 7.81-8.81 (Ar, 6H), 5.43 (m, 1H), 3.94 (m, 1H), 3.82 (m, 1H), 2.64 (m, 1H), 2.20-2.32 (m, 6H).

Example 8

Preparation of Compound 43

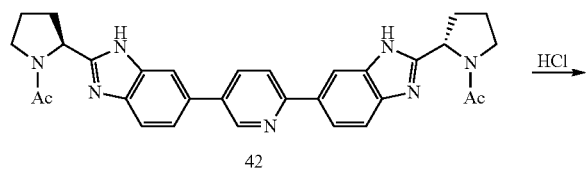

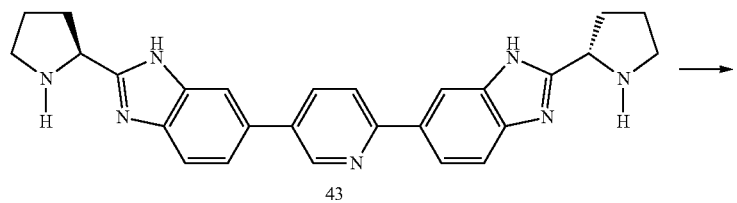

A solution of compound 42 (40 mg, 0.08 mmol) in 6N HCl (4 mL) was heated to reflux and allowed to stir at this temperature for 2 hours. The reaction mixture was then cooled to room temperatured, concentrated in vacuo and the residue obtained was dried under high vacuum to provide compound 43 (40 mg) as its HCl salt. (MS: MH⁺=450.2).

Example 9

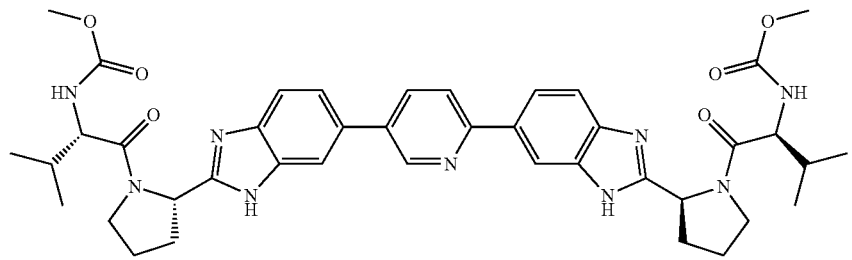

Preparation of Compound 44

To a solution of compound 43 (22 mg, 0.048 mmol), compound Int-1a (21 g, 0.11 mmol) and HATU (37 mg, 0.096 mmol) in anhydrous DMF (2 mL) was added diisopropylethylamine (Hunig's base, 45 μL, 0.24 mmol) dropwise and the reaction was allowed to stir at room temperature for 14 hours. The reaction mixture was then concentrated in vacuo and the residue obtained was purified using reverse phase HPLC (Acetonitrile/H₂O) to provide compound 44 (11 mg, 30%). LCMS: MH⁺=764.4.

Example 10

Preparation of Compound 129

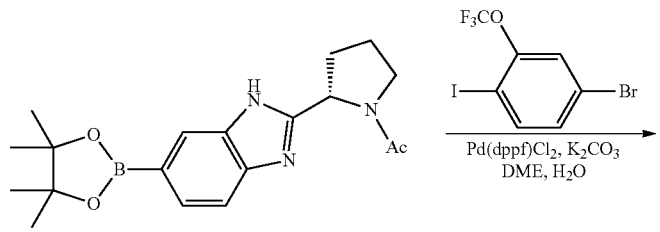

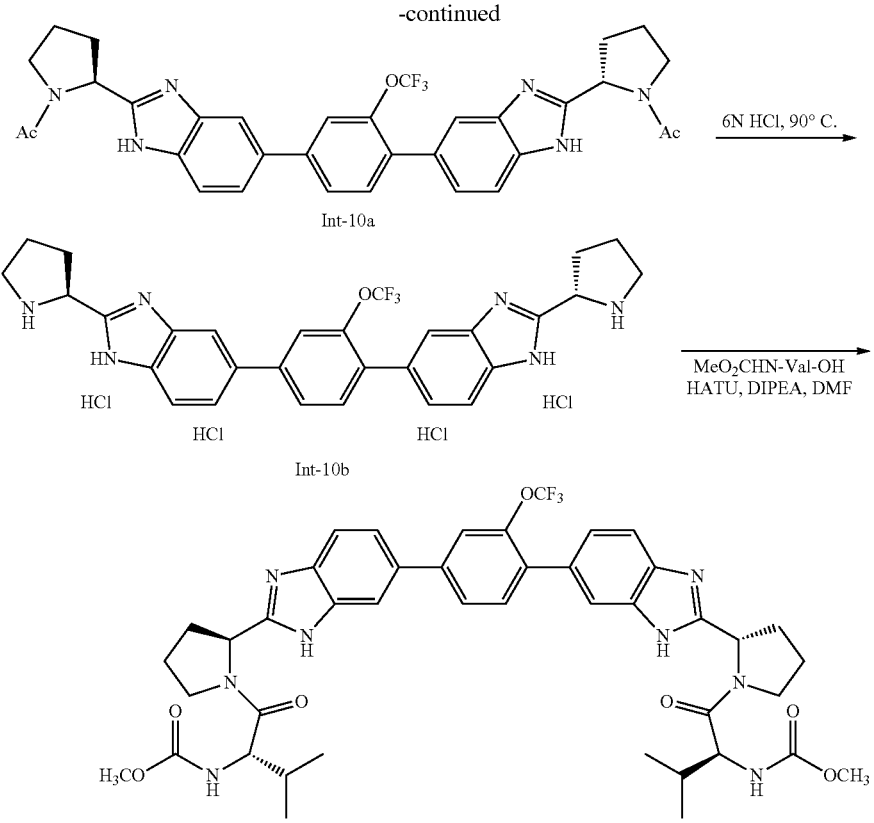

Step A—Synthesis of Compound Int-10a

A 250 mL round bottomed flask was charged with 4-iodo-3-trifluoromethoxy bromobenzene (2 g, 5.5 mmol), DME (50 mL), Pd (dppf)$_2$Cl$_2$ and degassed by flushing with nitrogen three times. Compound Int-6c (3.9 g, 11 mmol) was added followed by a solution of potassium carbonate (2.3 g, 16.5 mmol) in 15 mL water. The resulting reaction was allowed to stir for 1 hour, then was filtered and the filtrate concentrated in vacuo. The resulting residue was purified using flash column chromatography on silica gel (gradient elution: methylene chloride:Methanol from 0 to 10% MeOH) to provide compound Int-10a (2 g).

Step B—Synthesis of Compound Int-10b

Compound Int-10a (2.0 g, 3.8 mmol) was dissolved in 6 N HCl (30 mL) and the resulting reaction was heated to 90° C. and allowed to stir at this temperature for 8 hours. The reaction mixture was then cooled to room temperature and concentrated in vacuo to provide compound Int-10b which was used without further purification.

Step C—Synthesis of Compound 129

To a solution of compound Int-10b in 5 mL DMF was added MeO$_2$CHN-Val-OH (1.6 g, 9.12 mmol), HATU (2.9 g, 7.6 mmol) and Hunig's base (2.45 g, 19 mmol) and the reaction mixture was allowed to stir at room temperature for 1.5 hours. The reaction mixture was then concentrated in vacuo and the resulting residue was purified using reverse-phase HPLC (C18 Gemini 5 micron column, Gradient acetonitrile/water w/0.1% TFA) to provide the TFA salt of compound 129. The TFA salt was dissolved in dioxane and 1 N HCl (2.1 mL) in dioxane was added. The resulting solution was then concentrated in vacuo to provide the HCl salt of compound 129 (1.8 g). MS (M+) 847 amu.

Compounds 55, 59, 64, 72, 91, 99, 103, 115, 117, 119, 121, 128, 133, 134, and 135 were prepared using methods similar to those described in the example described above.

Example 11

Cell-Based HCV Replicon Assay

To measure cell-based anti-HCV activity of selected compounds of the present invention, replicon cells were seeded at 5000 cells/well in 96-well collagen I-coated Nunc plates in the presence of the test compound. Various concentrations of test compound, typically in 10 serial 2-fold dilutions, were added to the assay mixture, with the starting concentration ranging from 250 µM to 1 µM. The final concentration of DMSO was 0.5%, fetal bovine serum was 5%, in the assay media. Cells were harvested on day 3 by the addition of 1× cell lysis buffer (Ambion cat #8721). The replicon RNA level was measured using real time PCR (Taqman assay). The amplicon was located in 5B. The PCR primers were: 5B.2F, ATGGACAGGCGCCCTGA (SEQ. ID NO. 1); 5B.2R, TTGATGGGCAGCTTGGTTTC (SEQ. ID NO. 2); the probe sequence was FAM-labeled CACGCCATGCGCTGCGG (SEQ. ID NO. 3). GAPDH RNA was used as endogenous control and was amplified in the same reaction as NS5B (multiplex PCR) using primers and VIC-labeled probe recommended by the manufacturer (PE Applied Biosystem). The real-time RT-PCR reactions were run on ABI PRISM 7900HT Sequence Detection System using the following program: 48° C. for 30 min, 95° C. for 10 min, 40 cycles of 95° C. for 15 sec, 60° C. for 1 min. The ACT values ($CT_{5B}$-$CT_{GAPDH}$) were plotted against the concentration of test compound and fitted to the sigmoid dose-response model using XLfit4 (MDL). $EC_{50}$ was defined as the concentration of inhibitor necessary to achieve $\Delta CT=1$ over the projected baseline; $EC_{90}$ the concentration necessary to achieve $\Delta CT=3.2$ over the baseline. Alternatively, to quantitate the absolute amount of replicon RNA, a standard curve was established by including serially diluted T7 transcripts of replicon RNA in the Taqman assay. All Taqman reagents were from PE Applied Biosystems. Such an assay procedure was described in detail in e.g. Malcolm et al., *Antimicrobial Agents and Chemotherapy* 50: 1013-1020 (2006).

To date, compounds in different structural classes acting on different sites within the HCV polyprotein have demonstrated efficacy in various species, including humans, in reducing HCV viral titers. Furthermore, the subgenomic replicon assay is highly correlated with efficacy in non-humans and humans infected with HCV. See K. del Carmen et al., *Annals of Hepatology,* 2004, 3:54.

It is accepted that the HCV replicon system described above is useful for the development and the evaluation of antiviral drugs. See Pietschmann, T. & Bartenschlager, R., *Current Opinion in Drug Discovery Research* 2001, 4:657-664).

HCV replicon assay data was calculated for selected compounds of the present invention using this method. $EC_{90}$ data for selected compounds of the present invention is provided in the table below wherein A is <1 nM, B is 1-999 nM, and C is >1000 nM.

| Compound number | Structure | Analytical Data | Biological Activity |
|---|---|---|---|
| 42 | 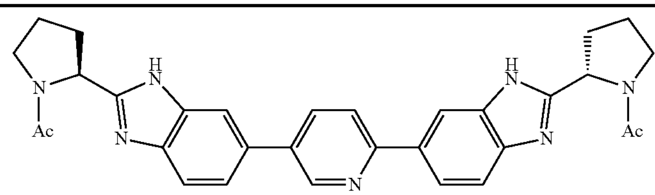 | $(M+H)^+$: 534.3 | C |
| 43 | 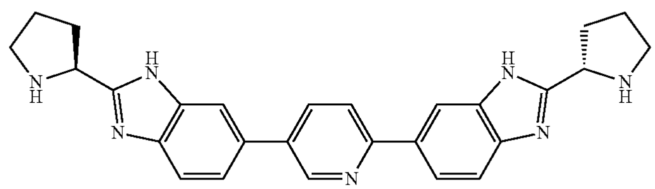 [SMILES: c1cc(-c2ccc3nc([C@@H]4CCCN4)[nH]c3c2)ncc1-c1ccc2nc([C@@H]3CCCN3)[nH]c2c1] | $(M+H)^+$: 450.2 | C |
| 44 | 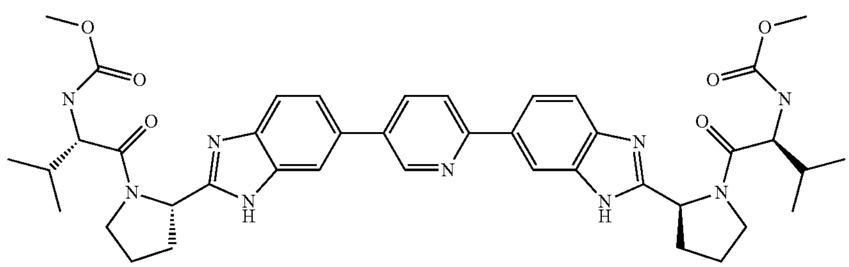 [SMILES: COC(=O)N[C@H](C(=O)N1CCC[C@H]1c1nc2ccc(-c3ccc(-c4ccc5nc([C@@H]6CCCN6C(=O)[C@@H](NC(=O)OC)C(C)C)[nH]c5c4)nc3)cc2[nH]1)C(C)C] | $(M+H)^+$: 764.4 | A |
| 55 | 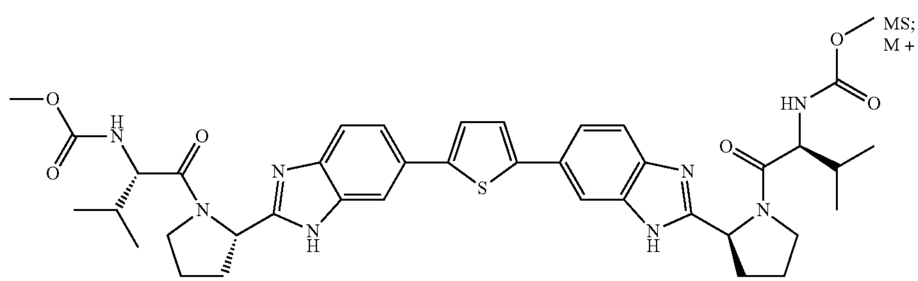 | MS; M + H = 769.9 | A |
| 59 | 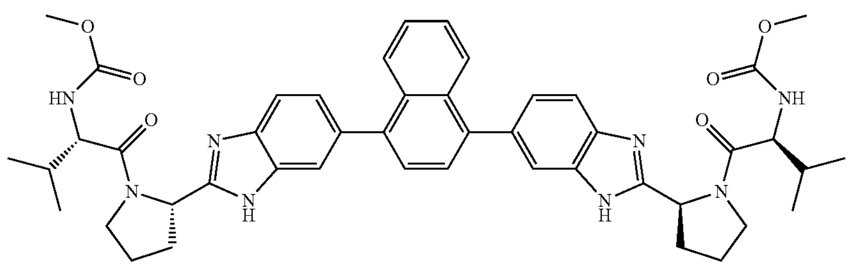 [SMILES: COC(=O)N[C@H](C(=O)N1CCC[C@H]1c1nc2ccc(-c3ccc(-c4ccc5nc([C@@H]6CCCN6C(=O)[C@@H](NC(=O)OC)C(C)C)[nH]c5c4)c4ccccc34)cc2[nH]1)C(C)C] | MS; M + H = 814 | A |

-continued

| Compound number | Structure | Analytical Data | Biological Activity |
|---|---|---|---|
| 64 | 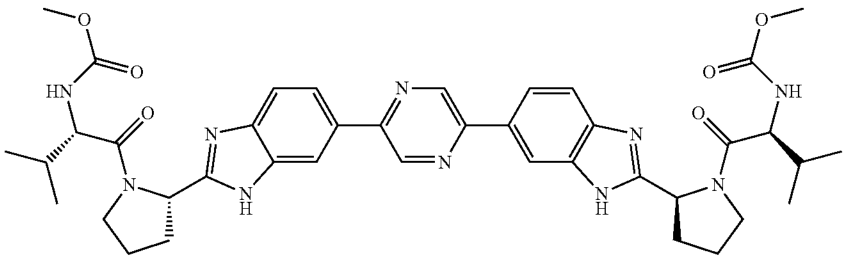 [SMILES: COC(=O)N[C@H](C(=O)N1CCC[C@H]1c1nc2ccc(-c3cnc(-c4ccc5nc([C@@H]6CCCN6C(=O)[C@@H](NC(=O)OC)C(C)C)[nH]c5c4)cn3)cc2[nH]1)C(C)C] | MS; M + H = 765.9 | A |
| 72 | 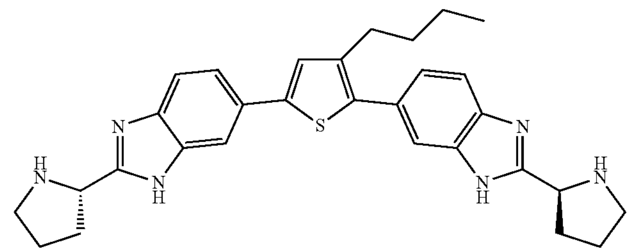 [SMILES: CCCCc1cc(-c2ccc3nc([C@@H]4CCCN4)[nH]c3c2)sc1-c1ccc2nc([C@@H]3CCCN3)[nH]c2c1] | MS; M + H = 511.7 | 26 nM |
| 91 | 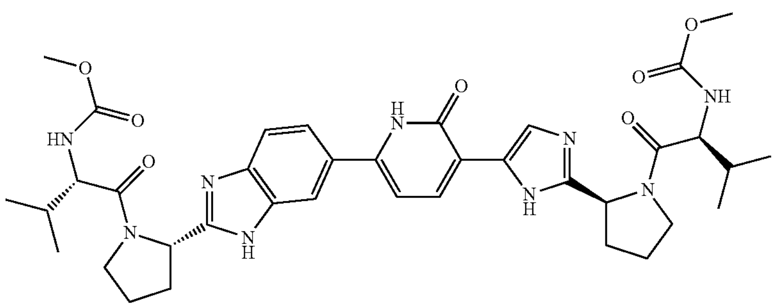 [SMILES: COC(=O)N[C@H](C(=O)N1CCC[C@H]1c1ncc(-c2ccc(-c3ccc4nc([C@@H]5CCCN5C(=O)[C@@H](NC(=O)OC)C(C)C)[nH]c4c3)[nH]c2=O)[nH]1)C(C)C] | MS; M + H = 731 | 6 nM |
| 99 | 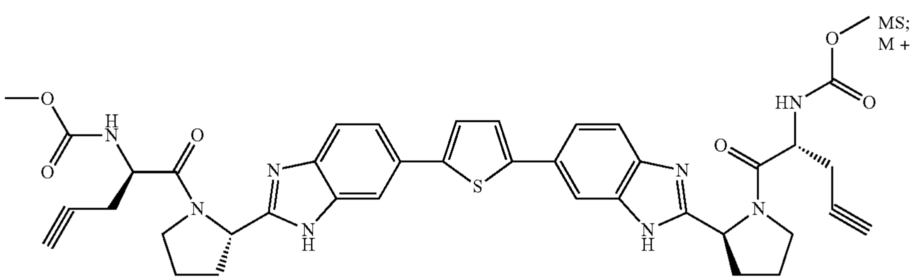 | MS; M + H = 761.9 | 0.2 |
| 103 | 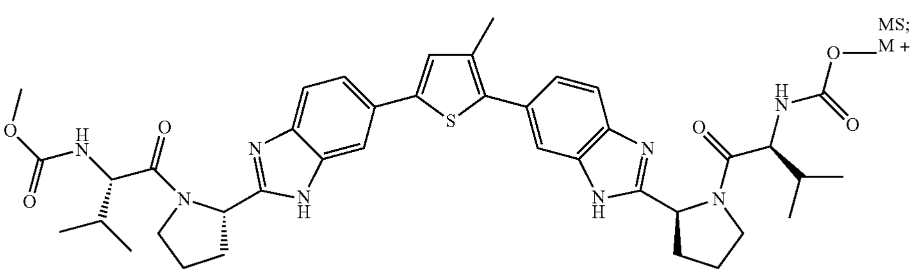 | MS; M + H = 784.1 | 0.005 |

| Compound number | Structure | Analytical Data | Biological Activity |
|---|---|---|---|
| 115 | 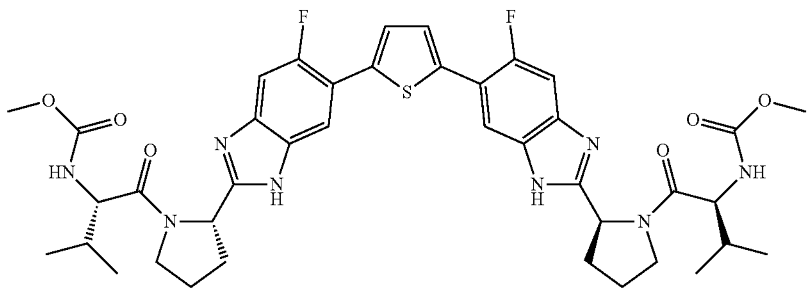 | MS; M + H = 806 | .003 |
| 117 | 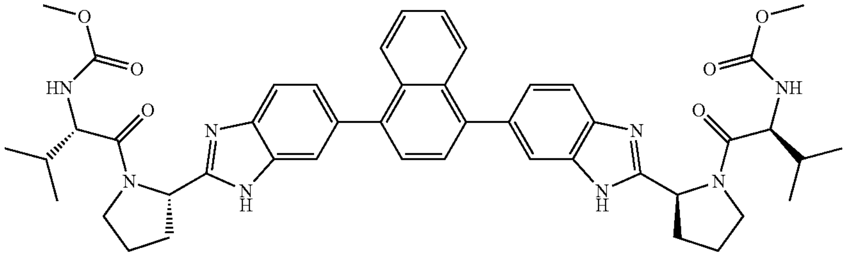 [SMILES: COC(=O)N[C@H](C(=O)N1CCC[C@H]1c1nc2ccc(-c3ccc(-c4ccc5nc([C@@H]6CCCN6C(=O)[C@@H](NC(=O)OC)C(C)C)[nH]c5c4)c4ccccc34)cc2[nH]1)C(C)C] | MS; M + H = 814 | A |
| 119 | 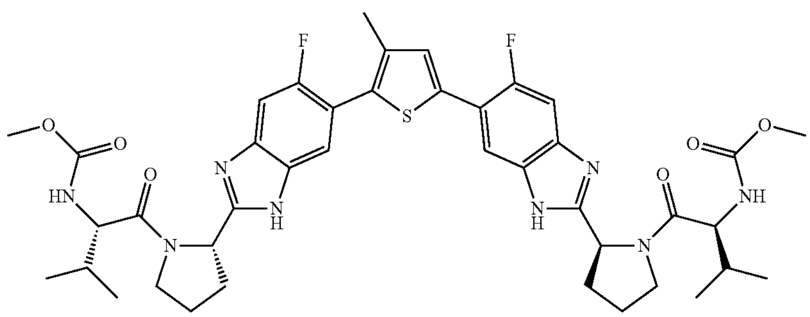 | MS; M + H = 820 | A |
| 121 | 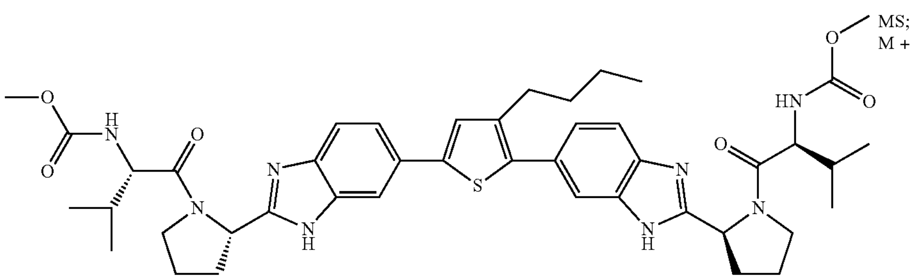 | MS; M + H = 826.1 | A |
| 128 | 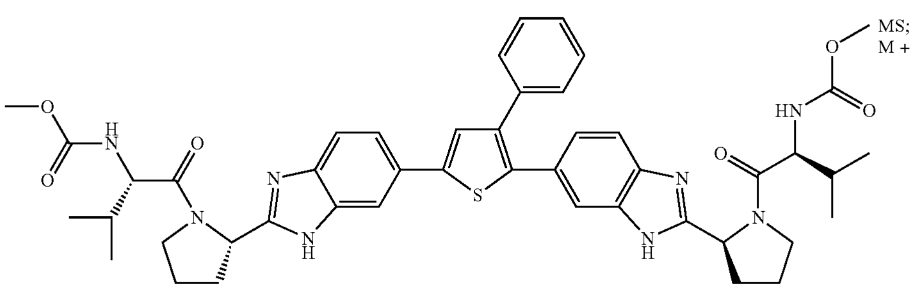 | MS; M + H = 846 | A |

-continued

| Compound number | Structure | Analytical Data | Biological Activity |
|---|---|---|---|
| 129 | 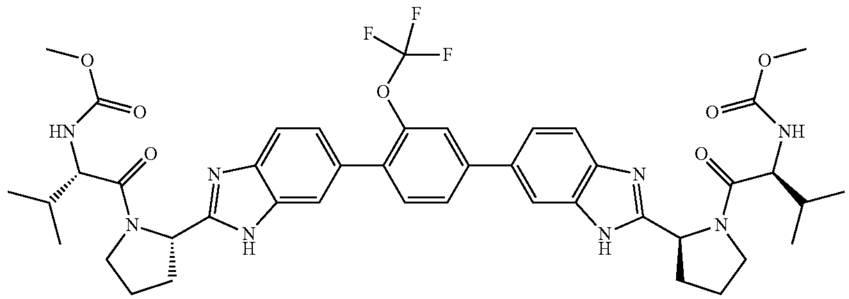 [SMILES: COC(=O)N[C@H](C(=O)N1CCC[C@H]1c1nc2ccc(-c3ccc(-c4ccc5nc([C@@H]6CCCN6C(=O)[C@@H](NC(=O)OC)C(C)C)[nH]c5c4)c(OC(F)(F)F)c3)cc2[nH]1)C(C)C] | MS; M + H = 848 | A |
| 133 | 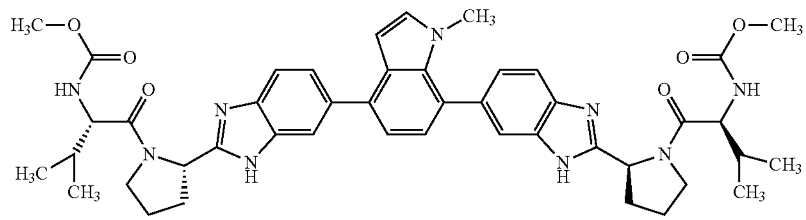 | MS; M + H = 816.5 | A |
| 134 | 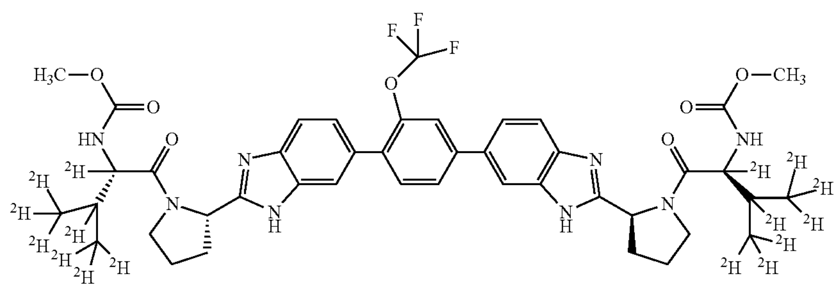 [SMILES: [2H]C([2H])([2H])C([2H])(C([2H])([2H])[2H])[C@]([2H])(NC(=O)OC)C(=O)N1CCC[C@H]1c1nc2ccc(-c3ccc(-c4ccc5nc([C@@H]6CCCN6C(=O)[C@@]([2H])(NC(=O)OC)C([2H])(C([2H])([2H])[2H])C([2H])([2H])[2H])[nH]c5c4)c(OC(F)(F)F)c3)cc2[nH]1] | MS; M + H = 863.5 | A |
| 135 | 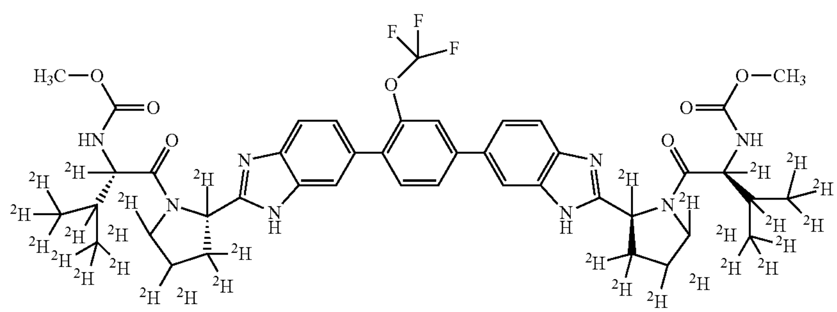 | MS; M + H = 877.6 | A |

HCV replicon assay data (EC$_{50}$ data) was calculated for genotypes 1a 1A7 and 1b c16 for compound 129, and is as follows: 0.05 nM (1a 1A7) and 0.003 nM (1b c16). Compound 129-dihydrochloride salt exhibited an oral bioavailability of 23% when dosed in C. Monkeys (0.4% MC, 3 mpk).

Uses of the Tricyclic Compounds

The Tricyclic Compounds are useful in human and veterinary medicine for treating or preventing a viral infection in a patient. In one embodiment, the Tricyclic Compounds can be inhibitors of viral replication. In another embodiment, the Tricyclic Compounds can be inhibitors of HCV replication. Accordingly, the Tricyclic Compounds are useful for treating viral infections, such as HCV. In accordance with the invention, the Tricyclic Compounds can be administered to a patient in need of treatment or prevention of a viral infection.

Accordingly, in one embodiment, the invention provides methods for treating a viral infection in a patient comprising administering to the patient an effective amount of at least one Tricyclic Compound or a pharmaceutically acceptable salt thereof.

Treatment or Prevention of a Flaviviridae Virus

The Tricyclic Compounds can be useful for treating or preventing a viral infection caused by the Flaviviridae family of viruses.

Examples of Flaviviridae infections that can be treated or prevented using the present methods include but are not limited to, dengue fever, Japanese encephalitis, Kyasanur Forest disease, Murray Valley encephalitis, St. Louis encephalitis, Tick-borne encephalitis, West Nile encephalitis, yellow fever and Hepatitis C Virus (HCV) infection.

In one embodiment, the Flaviviridae infection being treated is hepatitis C virus infection.

Treatment or Prevention of HCV Infection

Without being bound by any specific mechanism, the Tricyclic Compounds are useful in the inhibition of HCV (e.g., HCV replicon activity), the treatment of HCV infection and/or reduction of the likelihood or severity of symptoms of HCV infection and the inhibition of HCV viral replication and/or HCV viral production in a cell-based system. For example, the Tricyclic Compounds are useful in treating infection by HCV after suspected past exposure to HCV by such means as blood transfusion, exchange of body fluids, bites, accidental needle stick, or exposure to patient blood during surgery or other medical procedures.

In one embodiment, the hepatitis C infection is acute hepatitis C. In another embodiment, the hepatitis C infection is chronic hepatitis C.

Accordingly, in one embodiment, the invention provides methods for treating HCV infection in a patient, the methods comprising administering to the patient an effective amount of at least one Tricyclic Compound or a pharmaceutically acceptable salt thereof. In a specific embodiment, the amount administered is effective to treat or prevent infection by HCV in the patient. In another specific embodiment, the amount administered is effective to inhibit HCV viral replication and/or viral production in the patient.

The Tricyclic Compounds are also useful in the preparation and execution of screening assays for antiviral compounds. For example the Tricyclic Compounds are useful for identifying resistant HCV replicon cell lines harboring mutations within NS5A, which are excellent screening tools for more powerful antiviral compounds. Furthermore, the Tricyclic Compounds are useful in establishing or determining the binding site of other antivirals to the HCV replicase.

The compositions and combinations of the present invention can be useful for treating a patient suffering from infection related to any HCV genotype. HCV types and subtypes may differ in their antigenicity, level of viremia, severity of disease produced, and response to interferon therapy as described in Holland et al., *Pathology*, 30(2):192-195 (1998). The nomenclature set forth in Simmonds et al., *J Gen Virol*, 74(Pt1):2391-2399 (1993) is widely used and classifies isolates into six major genotypes, 1 through 6, with two or more related subtypes, e.g., 1a and 1b. Additional genotypes 7-10 and 11 have been proposed, however the phylogenetic basis on which this classification is based has been questioned, and thus types 7, 8, 9 and 11 isolates have been reassigned as type 6, and type 10 isolates as type 3 (see Lamballerie et al., *J Gen Virol*, 78(Pt1):45-51 (1997)). The major genotypes have been defined as having sequence similarities of between 55 and 72% (mean 64.5%), and subtypes within types as having 75%-86% similarity (mean 80%) when sequenced in the NS-5 region (see Simmonds et al., *J Gen Virol*, 75(Pt 5):1053-1061 (1994)).

Combination Therapy

In another embodiment, the present methods for treating or preventing HCV infection can further comprise the administration of one or more additional therapeutic agents which are not Tricyclic Compounds.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a patient, the method comprising administering to the patient: (i) at least one Tricyclic Compound, or a pharmaceutically acceptable salt thereof, and (ii) at least one additional therapeutic agent that is other than a Tricyclic Compound, wherein the amounts administered are together effective to treat or prevent a viral infection.

When administering a combination therapy of the invention to a patient, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Tricyclic Compound and an additional therapeutic agent may be present in fixed amounts (dosage amounts) in a single dosage unit (e.g., a capsule, a tablet and the like).

In one embodiment, the at least one Tricyclic Compound is administered during a time when the additional therapeutic agent(s) exert their prophylactic or therapeutic effect, or vice versa.

In another embodiment, the at least one Tricyclic Compound and the additional therapeutic agent(s) are administered in doses commonly employed when such agents are used as monotherapy for treating a viral infection.

In another embodiment, the at least one Tricyclic Compound and the additional therapeutic agent(s) are administered in doses lower than the doses commonly employed when such agents are used as monotherapy for treating a viral infection.

In still another embodiment, the at least one Tricyclic Compound and the additional therapeutic agent(s) act synergistically and are administered in doses lower than the doses commonly employed when such agents are used as monotherapy for treating a viral infection.

In one embodiment, the at least one Tricyclic Compound and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that can be treated or prevented using the combination therapy methods of the present invention include, but are not limited to, those listed above.

In one embodiment, the viral infection is HCV infection.

The at least one Tricyclic Compound and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Tricyclic Compound and the additional therapeutic agent(s) may inhibit the resistance of a viral infection to these agents.

Non-limiting examples of additional therapeutic agents useful in the present compositions and methods include an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a virion production inhibitor, a viral entry inhibitor, a viral assembly inhibitor, an antibody therapy (monoclonal or polyclonal), and any agent useful for treating an RNA-dependent polymerase-related disorder.

In one embodiment, the additional therapeutic agent is a viral protease inhibitor.

In another embodiment, the additional therapeutic agent is a viral replication inhibitor.

In another embodiment, the additional therapeutic agent is an HCV NS3 protease inhibitor.

In still another embodiment, the additional therapeutic agent is an HCV NS5B polymerase inhibitor.

In another embodiment, the additional therapeutic agent is a nucleoside inhibitor.

In another embodiment, the additional therapeutic agent is an interferon.

In yet another embodiment, the additional therapeutic agent is an HCV replicase inhibitor.

In another embodiment, the additional therapeutic agent is an antisense agent.

In another embodiment, the additional therapeutic agent is a therapeutic vaccine.

In a further embodiment, the additional therapeutic agent is a virion production inhibitor.

In another embodiment, the additional therapeutic agent is an antibody therapy.

In another embodiment, the additional therapeutic agent is an HCV NS2 inhibitor.

In still another embodiment, the additional therapeutic agent is an HCV NS4A inhibitor.

In another embodiment, the additional therapeutic agent is an HCV NS4B inhibitor.

In another embodiment, the additional therapeutic agent is an HCV NS5A inhibitor.

In yet another embodiment, the additional therapeutic agent is an HCV NS3 helicase inhibitor.

In another embodiment, the additional therapeutic agent is an HCV IRES inhibitor.

In another embodiment, the additional therapeutic agent is an HCV p7 inhibitor.

In a further embodiment, the additional therapeutic agent is an HCV entry inhibitor.

In another embodiment, the additional therapeutic agent is an HCV assembly inhibitor.

In one embodiment, the additional therapeutic agents comprise a viral protease inhibitor and a viral polymerase inhibitor.

In still another embodiment, the additional therapeutic agents comprise a viral protease inhibitor and an immunomodulatory agent.

In yet another embodiment, the additional therapeutic agents comprise a polymerase inhibitor and an immunomodulatory agent.

In another embodiment, the additional therapeutic agents comprise a viral protease inhibitor and a nucleoside.

In another embodiment, the additional therapeutic agents comprise an immunomodulatory agent and a nucleoside.

In one embodiment, the additional therapeutic agents comprise an HCV protease inhibitor and an HCV polymerase inhibitor.

In another embodiment, the additional therapeutic agents comprise a nucleoside and an HCV NS5A inhibitor.

In another embodiment, the additional therapeutic agents comprise a viral protease inhibitor, an immunomodulatory agent and a nucleoside.

In a further embodiment, the additional therapeutic agents comprise a viral protease inhibitor, a viral polymerase inhibitor and an immunomodulatory agent.

In another embodiment, the additional therapeutic agent is ribavirin.

HCV polymerase inhibitors useful in the present compositions and methods include, but are not limited to, VP-19744 (Wyeth/ViroPharma), PSI-7851 (Pharmasset), R7128 (Roche/Pharmasset), PF-868554/filibuvir (Pfizer), VCH-759 (ViroChem Pharma), HCV-796 (Wyeth/ViroPharma), IDX-184 (Idenix), IDX-375 (Idenix), NM-283 (Idenix/Novartis), R-1626 (Roche), MK-0608 (Isis/Merck), INX-8014 (Inhibitex), INX-8018 (Inhibitex), INX-189 (Inhibitex), GS 9190 (Gilead), A-848837 (Abbott), ABT-333 (Abbott), ABT-072 (Abbott), A-837093 (Abbott), BI-207127 (Boehringer-Ingelheim), BILB-1941 (Boehringer-Ingelheim), MK-3281 (Merck), VCH222 (ViroChem), VCH916 (ViroChem), VCH716 (ViroChem), GSK-71185 (Glaxo SmithKline), ANA598 (Anadys), GSK-625433 (Glaxo SmithKline), XTL-2125 (XTL Biopharmaceuticals), and those disclosed in Ni et al., *Current Opinion in Drug Discovery and Development*, 7(4):446 (2004); Tan et al., *Nature Reviews*, 1:867 (2002); and Beaulieu et al., *Current Opinion in Investigational Drugs*, 5:838 (2004).

Other HCV polymerase inhibitors useful in the present compositions and methods include, but are not limited to, those disclosed in International Publication Nos. WO 08/082,484, WO 08/082,488, WO 08/083,351, WO 08/136,815, WO 09/032,116, WO 09/032,123, WO 09/032,124 and WO 09/032,125.

Interferons useful in the present compositions and methods include, but are not limited to, interferon alfa-2a, interferon alfa-2b, interferon alfacon-1 and PEG-interferon alpha conjugates. "PEG-interferon alpha conjugates" are interferon alpha molecules covalently attached to a PEG molecule. Illustrative PEG-interferon alpha conjugates include interferon alpha-2a (Roferon™, Hoffman La-Roche, Nutley, N.J.) in the form of pegylated interferon alpha-2a (e.g., as sold under the trade name Pegasys™), interferon alpha-2b (Intron™, from Merck) in the form of pegylated interferon alpha-2b (e.g., as sold under the trade name PEG-Intron™ from Merck), interferon alpha-2b-XL (e.g., as sold under the trade name PEG-Intron™), interferon alpha-2c (Berofor Alpha™, Boehringer Ingelheim, Ingelheim, Germany), PEG-interferon lambda (Bristol-Myers Squibb and ZymoGenetics), interferon alfa-2b alpha fusion polypeptides, interferon fused with the human blood protein albumin (Albuferon™, Human Genome Sciences), Omega Interferon (Intarcia), Locteron controlled release interferon (Biolex/OctoPlus), Biomed-510 (omega interferon), Peg-IL-29 (ZymoGenetics), Locteron CR (Octoplus), IFN-α-2b-XL (Flamel Technologies), and consensus interferon as defined by determination of a consensus sequence of naturally occurring interferon alphas (Infergen™, Amgen, Thousand Oaks, Calif.).

Antibody therapy agents useful in the present compositions and methods include, but are not limited to, antibodies specific to IL-10 (such as those disclosed in US Patent Publication No. US2005/0101770, humanized 12G8, a humanized monoclonal antibody against human IL-10, plasmids containing the nucleic acids encoding the humanized 12G8 light and heavy chains were deposited with the American Type Culture Collection (ATCC) as deposit numbers PTA-5923 and PTA-5922, respectively), and the like).

Examples of viral protease inhibitors useful in the present compositions and methods include, but are not limited to, an HCV protease inhibitor.

HCV protease inhibitors useful in the present compositions and methods include, but are not limited to, those disclosed in U.S. Pat. Nos. 7,494,988, 7,485,625, 7,449,447, 7,442,695, 7,425,576, 7,342,041, 7,253,160, 7,244,721, 7,205,330, 7,192,957, 7,186,747, 7,173,057, 7,169,760, 7,012,066, 6,914,122, 6,911,428, 6,894,072, 6,846,802, 6,838,475, 6,800,434, 6,767,991, 5,017,380, 4,933,443, 4,812,561 and 4,634,697; U.S. Patent Publication Nos. US20020068702, US20020160962, US20050119168, US20050176648, US20050209164, US20050249702 and US20070042968; and International Publication Nos. WO 03/006490, WO 03/087092, WO 04/092161 and WO 08/124148.

Additional HCV protease inhibitors useful in the present compositions and methods include, but are not limited to, SCH503034 (Boceprevir, Merck), SCH900518 (Merck), VX-950 (Telaprevir, Vertex), VX-500 (Vertex), VX-813 (Vertex), VBY-376 (Virobay), BI-201335 (Boehringer Ingelheim), TMC-435 (Medivir/Tibotec), ABT-450 (Abbott), MK-7009 (Merck), TMC-435350 (Medivir), ITMN-191/R7227 (InterMune/Roche), EA-058 (Abbott/Enanta), EA-063 (Abbott/Enanta), GS-9132 (Gilead/Achillion), ACH-1095 (Gilead/Achillon), IDX-136 (Idenix), IDX-316 (Idenix), ITMN-8356 (InterMune), ITMN-8347 (InterMune), ITMN-8096 (InterMune), ITMN-7587 (InterMune), PHX1766 (Phenomix), amprenavir, atazanavir, fosemprenavir, indinavir, lopinavir, ritonavir, nelfinavir, saquinavir, tipranavir, Kaletra (a combination of ritonavir and lopinavir) and TMC114.

Additional examples of HCV protease inhibitors useful in the present compositions and methods include, but are not limited to, those disclosed in Landro et al., *Biochemistry*, 36(31):9340-9348 (1997); Ingallinella et al., *Biochemistry*, 37(25):8906-8914 (1998); Llinàs-Brunet et al., *Bioorg Med Chem Lett*, 8(13):1713-1718 (1998); Martin et al., *Biochemistry*, 37(33):11459-11468 (1998); Dimasi et al., *J Virol*, 71(10):7461-7469 (1997); Martin et al., *Protein Eng*, 10(5):607-614 (1997); Elzouki et al., *J Hepat*, 27(1):42-48 (1997); *BioWorld Today*, 9(217):4 (Nov. 10, 1998); U.S. Patent Publication Nos. US2005/0249702 and US 2007/0274951; and International Publication Nos. WO 98/14181, WO 98/17679, WO 98/17679, WO 98/22496 and WO 99/07734 and WO 05/087731.

Further examples of HCV protease inhibitors useful in the present compositions and methods include, but are not limited to, the following compounds:

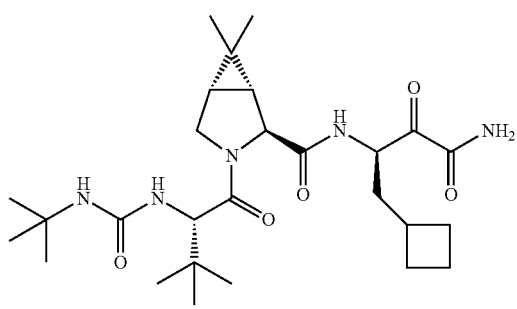

-continued

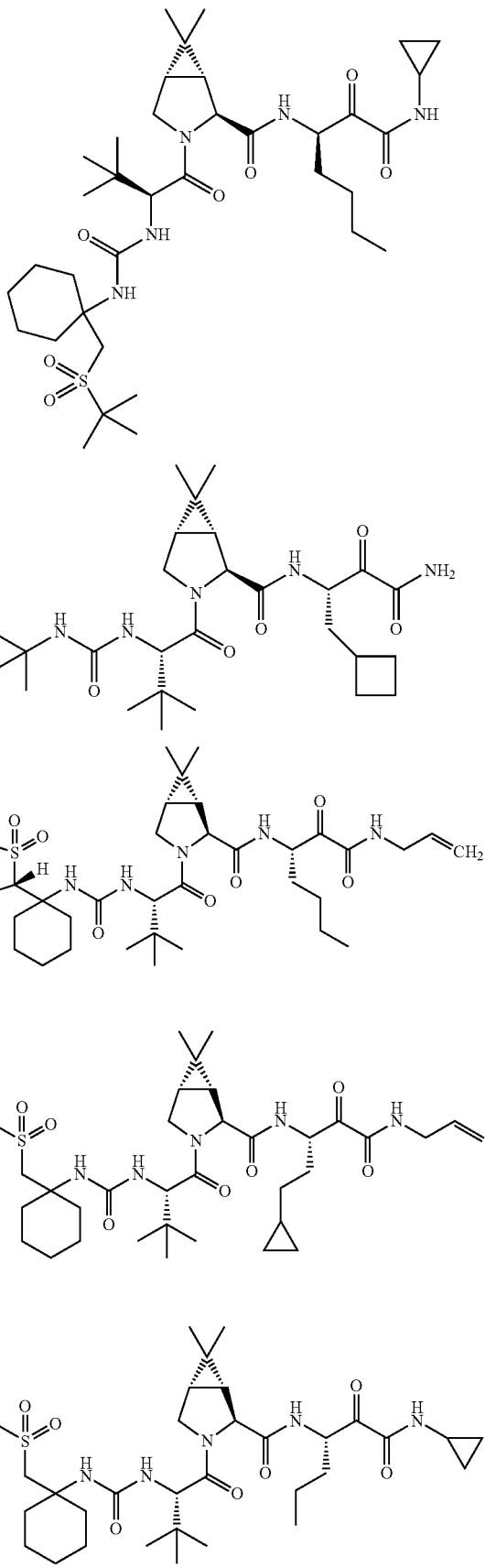

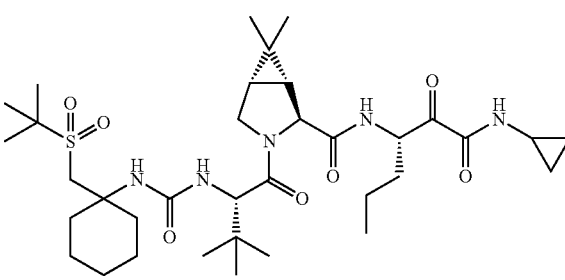

65
-continued
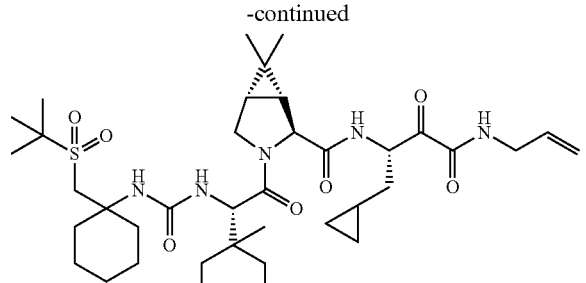
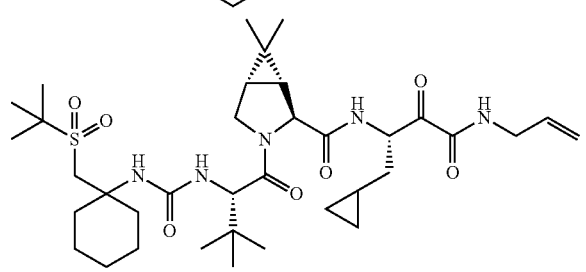
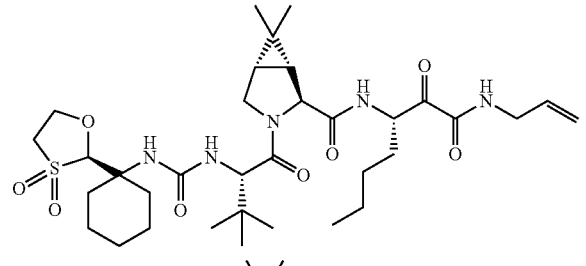
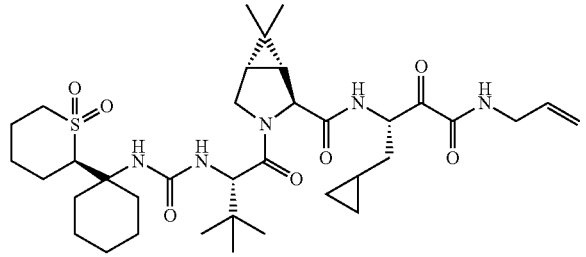
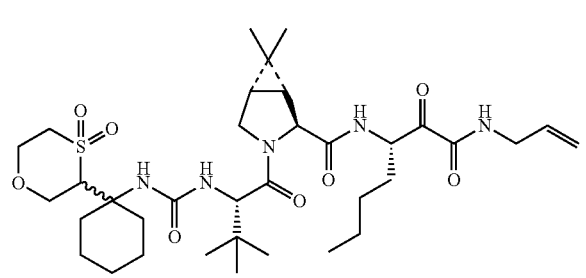
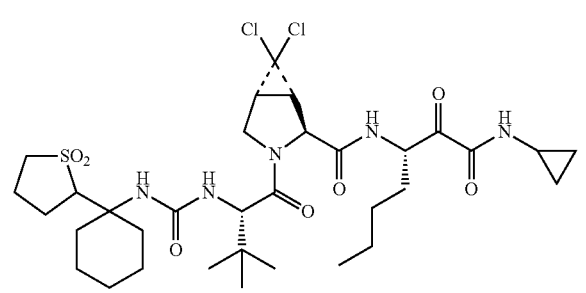
66
-continued
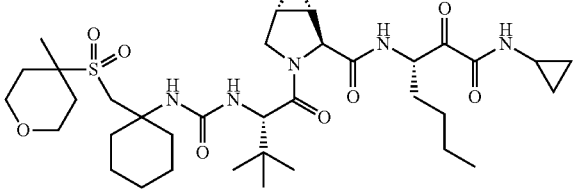
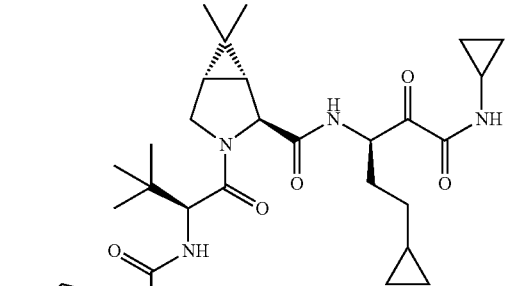
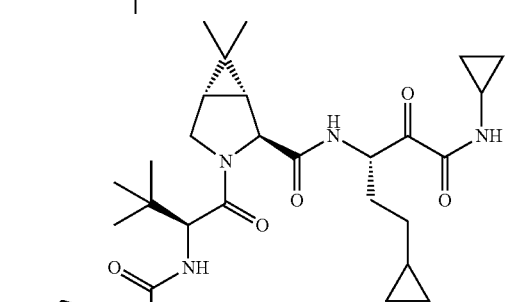
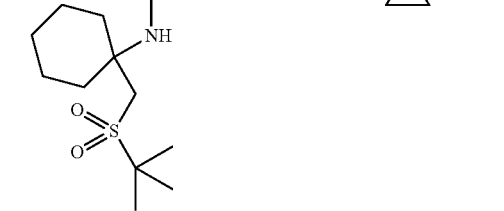
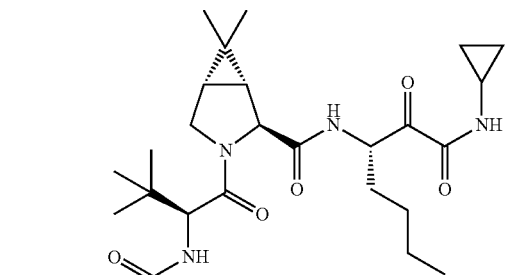
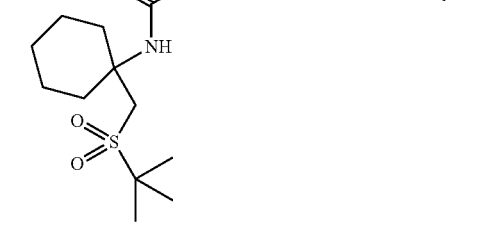

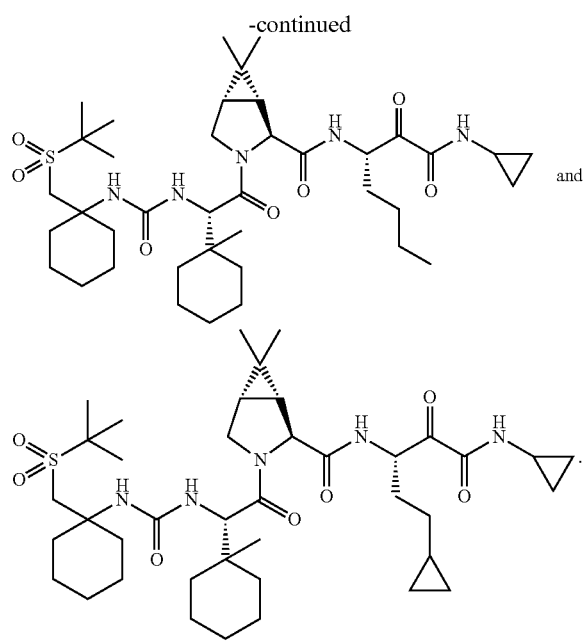

and

Viral replication inhibitors useful in the present compositions and methods include, but are not limited to, HCV replicase inhibitors, IRES inhibitors, NS4A inhibitors, NS3 helicase inhibitors, NS5A inhibitors, NS5B inhibitors, ribavirin, AZD-2836 (Astra Zeneca), BMS-790052 (Bristol-Myers Squibb), viramidine, A-831 (Arrow Therapeutics); an antisense agent or a therapeutic vaccine.

HCV NS4A inhibitors useful in the useful in the present compositions and methods include, but are not limited to, those disclosed in U.S. Pat. Nos. 7,476,686 and 7,273,885; U.S. Patent Publication No. US20090022688; and International Publication Nos. WO 2006/019831 and WO 2006/019832. Additional HCV NS4A inhibitors useful in the useful in the present compositions and methods include, but are not limited to, AZD2836 (Astra Zeneca) and ACH-806 (Achillon Pharmaceuticals, New Haven, Conn.).

HCV replicase inhibitors useful in the useful in the present compositions and methods include, but are not limited to, those disclosed in U.S. Patent Publication No. US20090081636.

Therapeutic vaccines useful in the present compositions and methods include, but are not limited to, IC41 (Intercell Novartis), CSL123 (Chiron/CSL), GI 5005 (Globeimmune), TG-4040 (Transgene), GNI-103 (GENimmune), Hepavaxx C (ViRex Medical), ChronVac-C (Inovio/Tripep), PeviPRO™ (Pevion Biotect), HCV/MF59 (Chiron/Novartis) and Civacir (NABI).

Examples of further additional therapeutic agents useful in the present compositions and methods include, but are not limited to, TT033 (Benitec/Tacere Bio/Pfizer), Sirna-034 (Sirna Therapeutics), GNI-104 (GENimmune), GI-5005 (GlobeImmune), IDX-102 (Idenix), Levovirin™ (ICN Pharmaceuticals, Costa Mesa, Calif.); Humax (Genmab), ITX-2155 (Ithrex/Novartis), PRO 206 (Progenics), HepaCide-I (NanoVirocides), MX3235 (Migenix), SCY-635 (Scynexis); KPE02003002 (Kemin Pharma), Lenocta (VioQuest Pharmaceuticals), IET—Interferon Enhancing Therapy (Transition Therapeutics), Zadaxin (SciClone Pharma), VP 50406™ (Viropharma, Incorporated, Exton, Pa.); Taribavirin (Valeant Pharmaceuticals); Nitazoxanide (Romark); Debio 025 (Debiopharm); GS-9450 (Gilead); PF-4878691 (Pfizer); ANA773 (Anadys); SCV-07 (SciClone Pharmaceuticals); NIM-881 (Novartis); ISIS 14803™ (ISIS Pharmaceuticals, Carlsbad, Calif.); Heptazyme™ (Ribozyme Pharmaceuticals, Boulder, Colo.); Thymosin™ (SciClone Pharmaceuticals, San Mateo, Calif.); Maxamine™ (Maxim Pharmaceuticals, San Diego, Calif.); NKB-122 (JenKen Bioscience Inc., North Carolina); Alinia (Romark Laboratories), INFORM-1 (a combination of R7128 and ITMN-191); and mycophenolate mofetil (Hoffman-LaRoche, Nutley, N.J.).

The doses and dosage regimen of the other agents used in the combination therapies of the present invention for the treatment or prevention of HCV infection can be determined by the attending clinician, taking into consideration the approved doses and dosage regimen in the package insert; the age, sex and general health of the patient; and the type and severity of the viral infection or related disease or disorder. When administered in combination, the Tricyclic Compound(s) and the other agent(s) can be administered simultaneously (i.e., in the same composition or in separate compositions one right after the other) or sequentially. This particularly useful when the components of the combination are given on different dosing schedules, e.g., one component is administered once daily and another every six hours, or when the preferred pharmaceutical compositions are different, e.g., one is a tablet and one is a capsule. A kit comprising the separate dosage forms is therefore advantageous.

Generally, a total daily dosage of the at least one Tricyclic Compound(s) alone, or when administered as combination therapy, can range from about 1 to about 2500 mg per day, although variations will necessarily occur depending on the target of therapy, the patient and the route of administration. In one embodiment, the dosage is from about 10 to about 1000 mg/day, administered in a single dose or in 2-4 divided doses. In another embodiment, the dosage is from about 1 to about 500 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In another embodiment, the dosage is from about 500 to about 1500 mg/day, administered in a single dose or in 2-4 divided doses. In still another embodiment, the dosage is from about 500 to about 1000 mg/day, administered in a single dose or in 2-4 divided doses. In yet another embodiment, the dosage is from about 100 to about 500 mg/day, administered in a single dose or in 2-4 divided doses.

In one embodiment, when the additional therapeutic agent is INTRON-A interferon alpha 2b (commercially available from Merck), this agent is administered by subcutaneous injection at 3MIU (12 mcg)/0.5 mL/TIW for 24 weeks or 48 weeks for first time treatment.

In another embodiment, when the additional therapeutic agent is PEG-INTRON interferon alpha 2b pegylated (commercially available from Merck), this agent is administered by subcutaneous injection at 1.5 mcg/kg/week, within a range of 40 to 150 mcg/week, for at least 24 weeks.

In another embodiment, when the additional therapeutic agent is ROFERON A interferon alpha 2a (commercially available from Hoffmann-La Roche), this agent is administered by subcutaneous or intramuscular injection at 3MIU (11.1 mcg/mL)/TIW for at least 48 to 52 weeks, or alternatively 6MIU/TIW for 12 weeks followed by 3MIU/TIW for 36 weeks.

In still another embodiment, when the additional therapeutic agent is PEGASUS interferon alpha 2a pegylated (commercially available from Hoffmann-La Roche), this agent is administered by subcutaneous injection at 180 mcg/1 mL or 180 mcg/0.5 mL, once a week for at least 24 weeks.

In yet another embodiment, when the additional therapeutic agent is INFERGEN interferon alphacon-1 (commercially available from Amgen), this agent is administered by subcutaneous injection at 9 mcg/TIW is 24 weeks for first time treatment and up to 15 mcg/TIW for 24 weeks for non-responsive or relapse treatment.

In a further embodiment, when the additional therapeutic agent is Ribavirin (commercially available as REBETOL ribavirin from Merck or COPEGUS ribavirin from Hoffmann-La Roche), this agent is administered at a daily dosage of from about 600 to about 1400 mg/day for at least 24 weeks.

In one embodiment, one or more compounds of the present invention are administered with one or more additional therapeutic agents selected from: an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a viral polymerase inhibitor a virion production inhibitor, a viral entry inhibitor, a viral assembly inhibitor, an antibody therapy (monoclonal or polyclonal), and any agent useful for treating an RNA-dependent polymerase-related disorder.

In another embodiment, one or more compounds of the present invention are administered with one or more additional therapeutic agents selected from an HCV protease inhibitor, an HCV polymerase inhibitor, an HCV replication inhibitor, a nucleoside, an interferon, a pegylated interferon and ribavirin. The combination therapies can include any combination of these additional therapeutic agents.

In another embodiment, one or more compounds of the present invention are administered with one additional therapeutic agent selected from an HCV protease inhibitor, an interferon, a pegylated interferon and ribavirin.

In still another embodiment, one or more compounds of the present invention are administered with two additional therapeutic agents selected from an HCV protease inhibitor, an HCV replication inhibitor, a nucleoside, an interferon, a pegylated interferon and ribavirin.

In another embodiment, one or more compounds of the present invention are administered with an HCV protease inhibitor and ribavirin. In another specific embodiment, one or more compounds of the present invention are administered with a pegylated interferon and ribavirin.

In another embodiment, one or more compounds of the present invention are administered with three additional therapeutic agents selected from an HCV protease inhibitor, an HCV replication inhibitor, a nucleoside, an interferon, a pegylated interferon and ribavirin.

In one embodiment, one or more compounds of the present invention are administered with one or more additional therapeutic agents selected from an HCV polymerase inhibitor, a viral protease inhibitor, an interferon, and a viral replication inhibitor. In another embodiment, one or more compounds of the present invention are administered with one or more additional therapeutic agents selected from an HCV polymerase inhibitor, a viral protease inhibitor, an interferon, and a viral replication inhibitor. In another embodiment, one or more compounds of the present invention are administered with one or more additional therapeutic agents selected from an HCV polymerase inhibitor, a viral protease inhibitor, an interferon, and ribavirin.

In one embodiment, one or more compounds of the present invention are administered with one additional therapeutic agent selected from an HCV polymerase inhibitor, a viral protease inhibitor, an interferon, and a viral replication inhibitor. In another embodiment, one or more compounds of the present invention are administered with ribavirin.

In one embodiment, one or more compounds of the present invention are administered with two additional therapeutic agents selected from an HCV polymerase inhibitor, a viral protease inhibitor, an interferon, and a viral replication inhibitor.

In another embodiment, one or more compounds of the present invention are administered with ribavirin, interferon and another therapeutic agent.

In another embodiment, one or more compounds of the present invention are administered with ribavirin, interferon and another therapeutic agent, wherein the additional therapeutic agent is selected from an HCV polymerase inhibitor, a viral protease inhibitor, and a viral replication inhibitor.

In still another embodiment, one or more compounds of the present invention are administered with ribavirin, interferon and a viral protease inhibitor.

In another embodiment, one or more compounds of the present invention are administered with ribavirin, interferon and an HCV protease inhibitor.

In another embodiment, one or more compounds of the present invention are administered with ribavirin, interferon and boceprevir or telaprevir.

In a further embodiment, one or more compounds of the present invention are administered with ribavirin, interferon and an HCV polymerase inhibitor.

Compositions and Administration

Due to their activity, the Tricyclic Compounds are useful in veterinary and human medicine. As described above, the Tricyclic Compounds are useful for treating or preventing HCV infection in a patient in need thereof.

When administered to a patient, the Tricyclic Compounds can be administered as a component of a composition that comprises a pharmaceutically acceptable carrier or vehicle. The present invention provides pharmaceutical compositions comprising an effective amount of at least one Tricyclic Compound and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Tricyclic Compounds are administered orally.

In another embodiment, the one or more Tricyclic Compounds are administered intravenously.

In another embodiment, the one or more Tricyclic Compounds are administered topically.

In still another embodiment, the one or more Tricyclic Compounds are administered sublingually.

In one embodiment, a pharmaceutical preparation comprising at least one Tricyclic Compound is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Tricyclic Compound(s) by weight or volume. In various embodiments, the present compositions can contain, in one embodiment, from about 1% to about 70% or from about 5% to about 60% of the Tricyclic Compound(s) by weight or volume.

The quantity of Tricyclic Compound in a unit dose of preparation may be varied or adjusted from about 1 mg to about 2500 mg. In various embodiment, the quantity is from about 10 mg to about 1000 mg, 1 mg to about 500 mg, 1 mg to about 100 mg, and 1 mg to about 100 mg.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the Tricyclic Compounds will be regulated according to the judgment of the attending clinician considering such factors as age, condition and size of the patient as well as severity of the symptoms being treated. Generally, a total daily dosage of the Tricyclic Compounds range from about 0.1 to about 2000 mg per day, although variations will necessarily occur depending on the target of therapy, the patient and the route of administration. In one embodiment, the dosage is from about 1 to about 200 mg/day, administered in a single dose or in 2-4 divided doses. In another embodiment, the dosage is from about 10 to about 2000 mg/day, administered in a single dose or in 2-4 divided doses. In another embodiment, the dosage is from about 100 to about 2000 mg/day, administered in a single dose or in 2-4 divided doses. In still another embodiment, the dosage is from about 500 to about 2000 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) at least one Tricyclic Compound or a pharmaceutically acceptable salt thereof; (ii) one or more additional therapeutic agents that are not a Tricyclic Compound; and (iii) a pharmaceutically acceptable carrier, wherein the amounts in the composition are together effective to treat HCV infection.

Kits

In one aspect, the present invention provides a kit comprising a therapeutically effective amount of at least one Tricyclic Compound, or a pharmaceutically acceptable salt of said compound and a pharmaceutically acceptable carrier, vehicle or diluent.

In another aspect the present invention provides a kit comprising an amount of at least one Tricyclic Compound, or a pharmaceutically acceptable salt of said compound and an amount of at least one additional therapeutic agent listed above, wherein the amounts of the two or more active ingredients result in a desired therapeutic effect. In one embodiment, the one or more Tricyclic Compounds and the one or more additional therapeutic agents are provided in the same container. In one embodiment, the one or more Tricyclic Compounds and the one or more additional therapeutic agents are provided in separate containers.

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A compound having the formula:

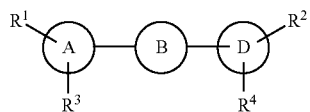

(I)

or a pharmaceutically acceptable salt thereof, wherein:

A is a 9- to 10-membered bicyclic heteroaryl containing one N atom and optionally, one to two additional heteroatoms independently selected from the group consisting of N, O, and S, wherein A is substituted on one ring carbon atom with $R^3$, and wherein A is optionally substituted on one to two ring carbon atoms with $R^{3a}$ and is optionally substituted on one ring nitrogen atom with $R^1$;

B is a ring selected from the group consisting of:

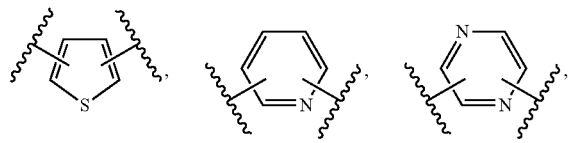

-continued

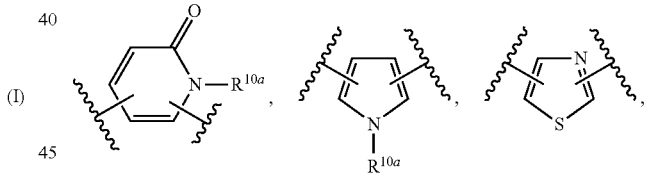

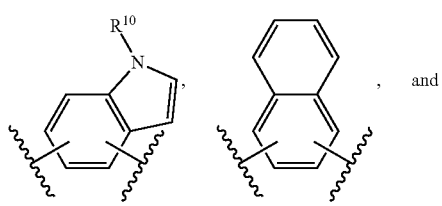

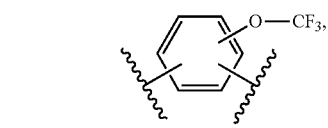

wherein B is optionally substituted on one or more ring carbon atoms by one to three $R^{10}$; and wherein when B is

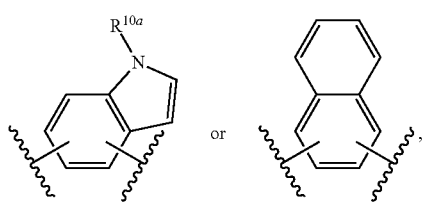 or , then A and D are each bonded to a common ring of B;

D is a 9 to 10-membered bicyclic heteroaryl containing one N atom and optionally, one to two additional heteroatoms independently selected from the group consisting of N, O, and S, wherein D is substituted on one ring carbon atom with $R^4$, and wherein D is optionally substituted on one two carbon atoms with $R^{4a}$ and is optionally substituted on one ring nitrogen atom with $R^2$;

$R^3$ and $R^4$ are independently selected from the group consisting of:

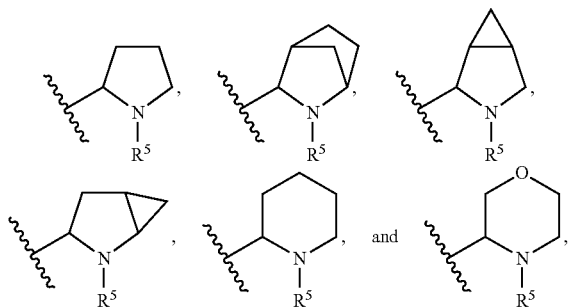

wherein $R^3$ and $R^4$ are optionally and independently substituted with:
(a) one to two fluorine or $C_1$-$C_3$ alkyl;
(b) and one to seven $^2H$;

each occurrence of $R^{3a}$ and $R^{4a}$ is independently selected from the group consisting of H, $C_1$-$C_3$ alkyl, $C_1$-$C_3$ alkoxy, halo, and $C_1$-$C_3$ trifluoroalkoxy;

$R^1$ and $R^2$ are independently H or $C_1$-$C_3$ alkyl;

each occurrence of $R^5$ is independently selected from the group consisting of:
(a) —C(O)—($C_1$-$C_6$ alkyl) optionally substituted by one to eight $R^{12}$ groups, wherein $R^{12}$ is selected from the group consisting of:
  (i) $C_1$-$C_3$ alkoxy,
  (ii) phenyl, optionally substituted by one to four halo, $C_1$-$C_3$ alkyl, or $C_1$-$C_3$ alkoxy;
  (iii) amino,
  (iv) $C_1$-$C_3$ monoalkylamino,
  (v) $C_1$-$C_3$ dialkylamino,
  (vi) —NHC(O)—O—($C_1$-$C_6$ alkyl),
  (vii) —N($C_1$-$C_3$ alkyl)—C(O)—O—($C_1$-$C_6$ alkyl),
  (viii) $C_1$-$C_3$ fluoroalkyl,
  (ix) $C_2$-$C_6$ alkynyl,
  (x) $C_3$-$C_7$ cycloalkyl,
  (xi) pyrrolidinyl,
  (xii) piperidinyl,
  (xiii) pyranyl; and
  (xiv) $^2H$;

(b) 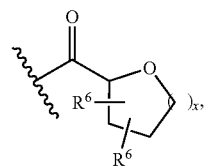

wherein x is 1 or 2, and each occurrence of $R^6$ is independently selected from the group consisting of H, $C_1$-$C_3$ alkyl, $C_1$-$C_3$ alkoxy, and fluoro; and
(c) H;

each occurrence of $R^{10}$ is independently $^2H$, halo, $C_1$-$C_6$ alkyl, $C_2$-$C_6$ alkenyl, $C_2$-$C_6$ alkynyl, $C_1$-$C_6$ alkoxy, cyano, and phenyl; and $R^{10a}$ is H or $C_1$-$C_6$ alkyl.

2. The compound of claim 1 or a pharmaceutically acceptable salt thereof, wherein B is selected from the group consisting of:

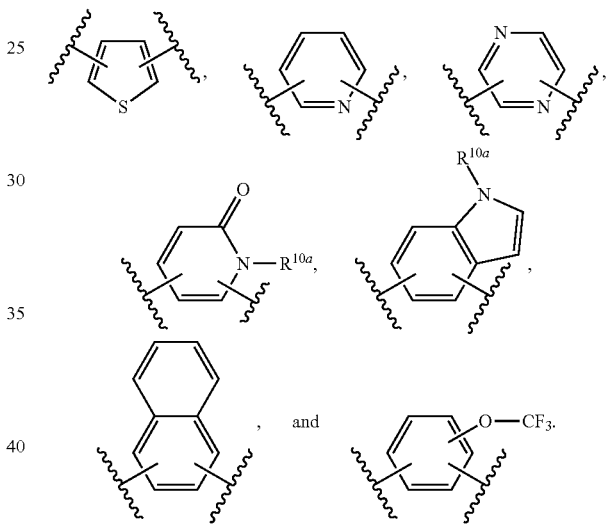

3. The compound of claim 1, or a pharmaceutically acceptable salt thereof, wherein A and D are each independently selected from the group consisting of:

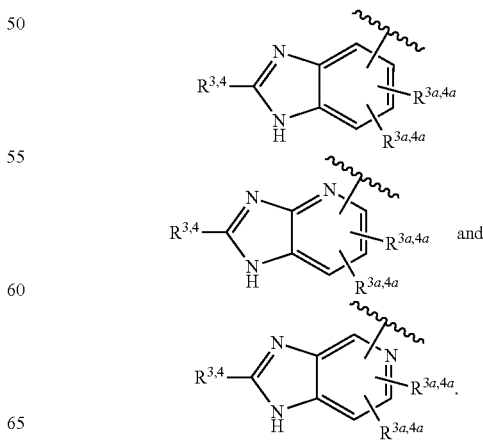

4. The compound of claim 1 or a pharmaceutically acceptable salt thereof, wherein $R^3$ and $R^4$ are independently selected from the group consisting of:

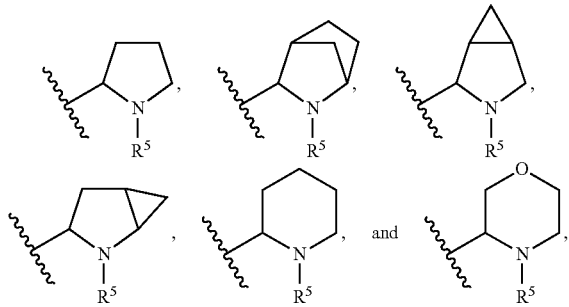

wherein $R^3$ and $R^4$ are optionally and independently substituted with one to two fluorine.

5. The compound of claim 1 or a pharmaceutically acceptable salt thereof, wherein each occurrence of $R^5$ is independently:

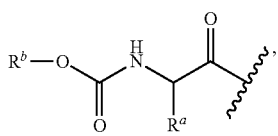

wherein $R^a$ is H, $C_1$-$C_4$ alkyl, $C_1$-$C_3$ fluoroalkyl, or phenyl, and $R^b$ is $C_1$-$C_3$ alkyl.

6. The compound of claim 1 or a pharmaceutically acceptable salt thereof, wherein each occurrence of $R^5$ is selected from the group consisting of:

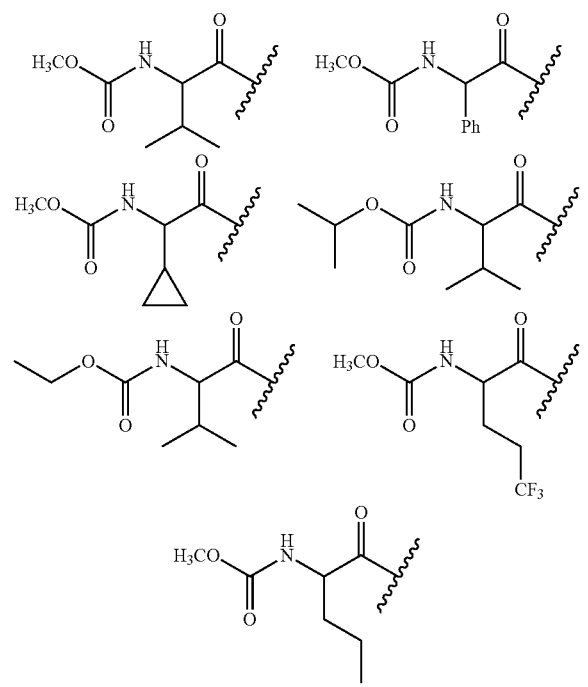

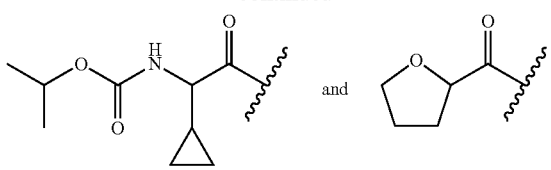

7. The compound of claim 1 or a pharmaceutically acceptable salt thereof, wherein A is benzimidazolyl, wherein said benzimidazolyl is optionally substituted on a ring carbon atom with one to two fluoro;

B is a ring selected from the group consisting of:

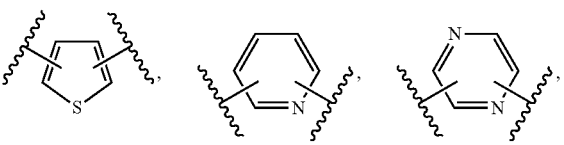

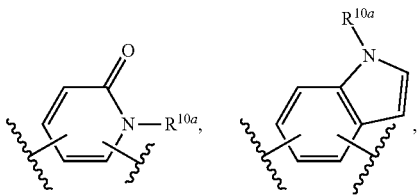

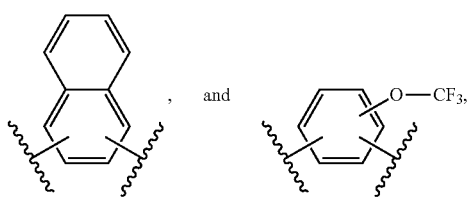

wherein B is optionally substituted on one or more ring carbon atoms by one to three $R^{10}$ and wherein when B is

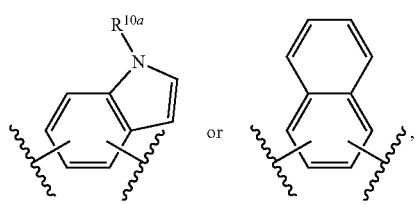

then A and D are each bonded to a common ring of B;

wherein $R^{10}$ is selected from the group consisting of H, $C_1$-$C_6$ alkyl and phenyl;

D is benzimidazolyl, wherein said benzimidazolyl is optionally substituted on a ring carbon atom with one to two fluoro;

$R^3$ and $R^4$ are independently selected from the group consisting of:

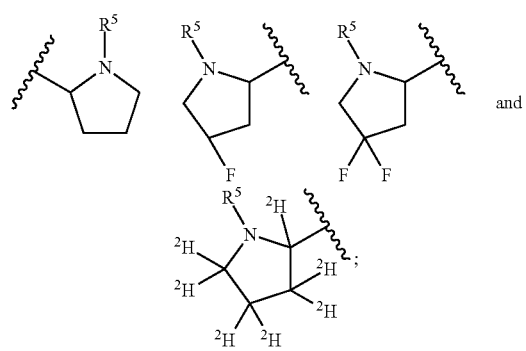

each occurrence of $R^5$ is independently selected from the group consisting of H and —C(O)—($C_1$-$C_6$ alkyl) optionally substituted by one to seven $R^{12}$ groups, wherein $R^{12}$ is selected from the group consisting of:
(i) —NHC(O)—O—($C_1$-$C_3$ alkyl)
(ii) $C_2$-$C_4$ alkynyl; and
(iii) $^2$H; and $R^{10a}$ is H or $C_1$-$C_3$ alkyl.

8. The compound of claim 7 or a pharmaceutically acceptable salt thereof, wherein A and D are independently selected from the group consisting of:

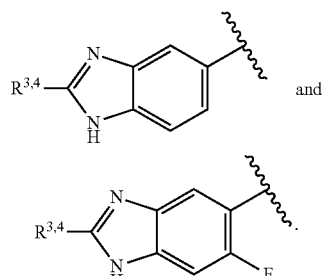

9. The compound of claim 8, or a pharmaceutically acceptable salt thereof, wherein $R^4$ are both

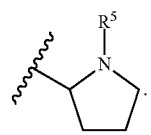

10. A compound selected from the group consisting of

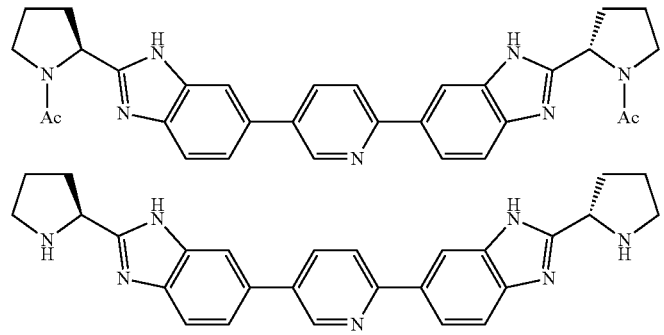

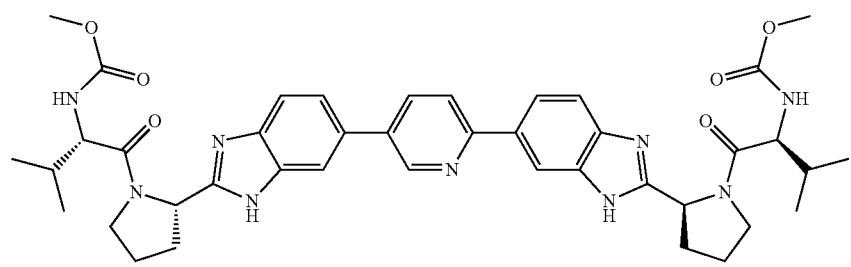

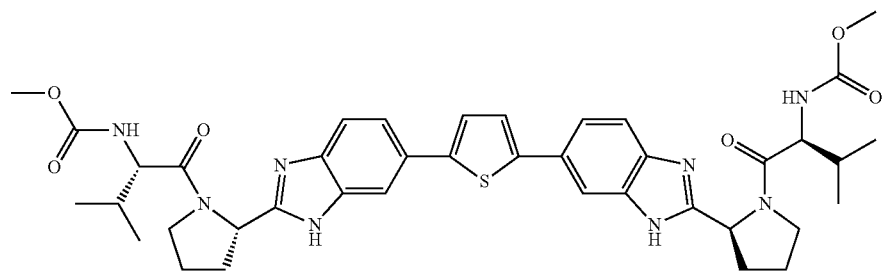

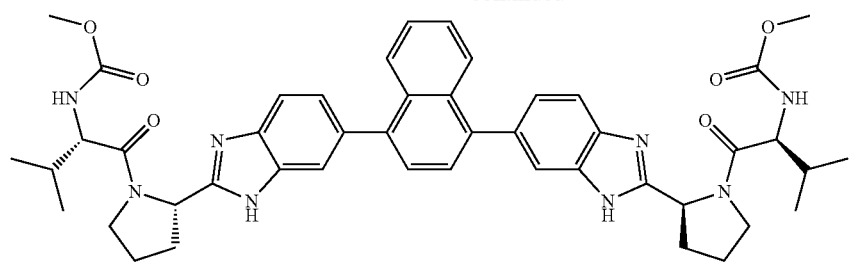
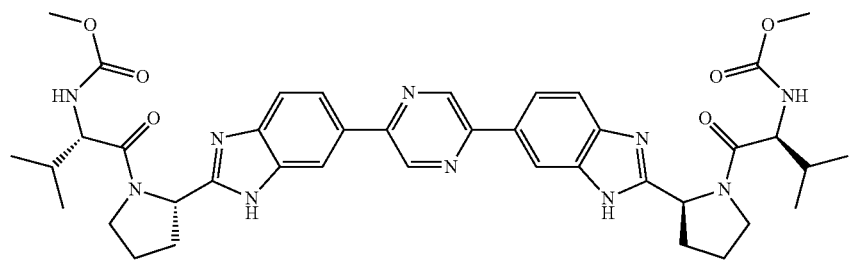
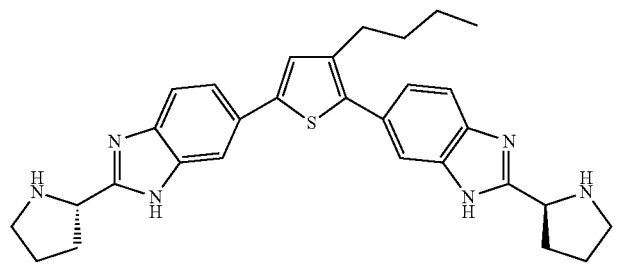
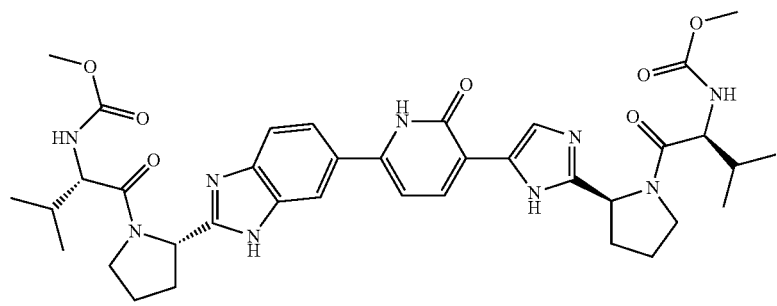
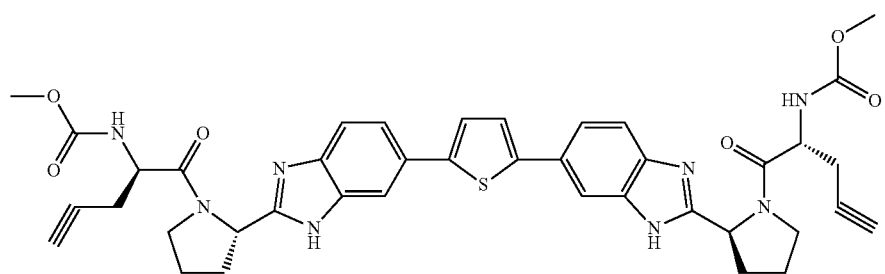
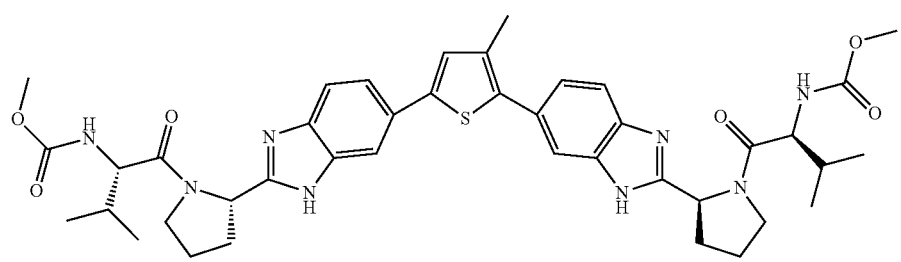

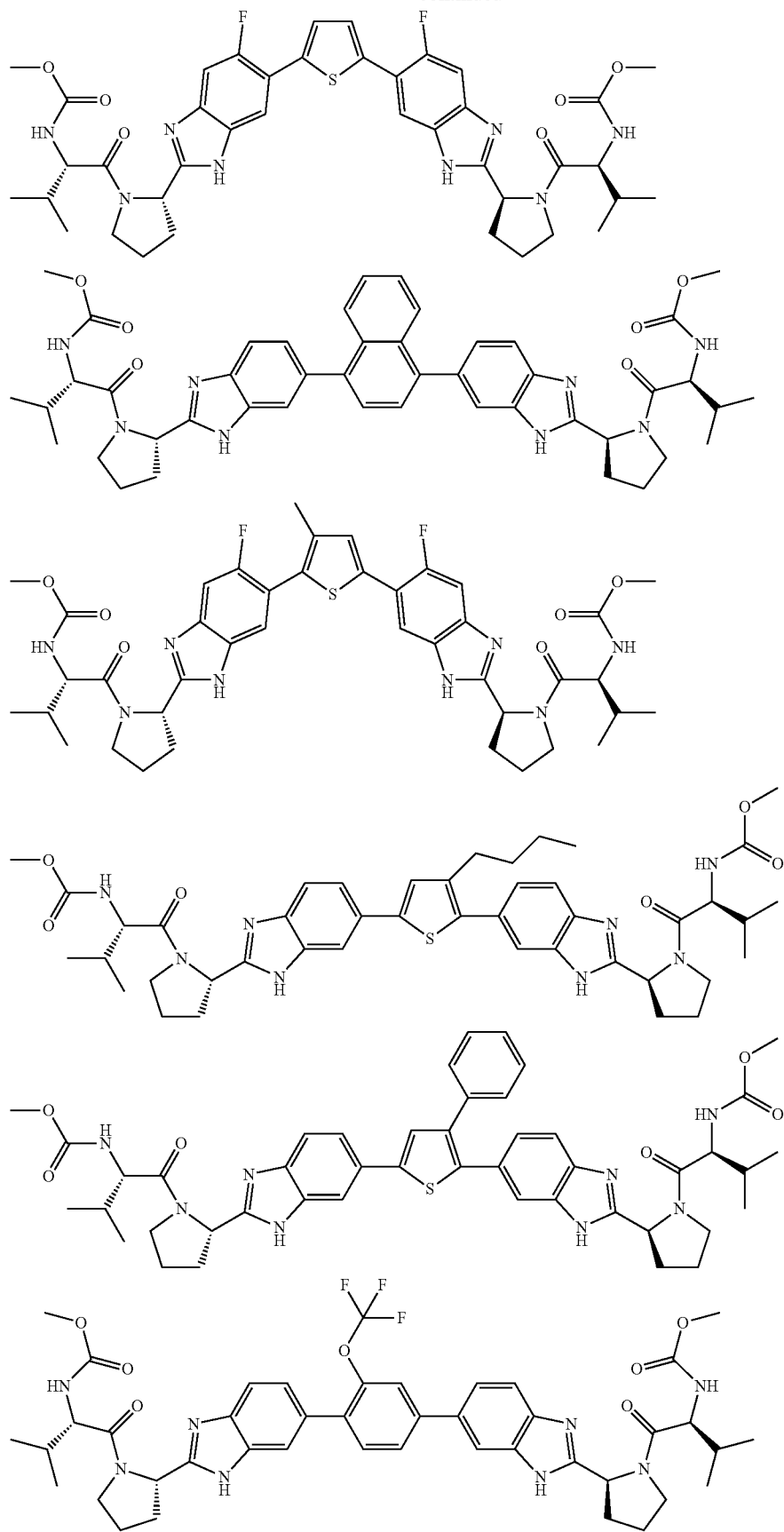

-continued
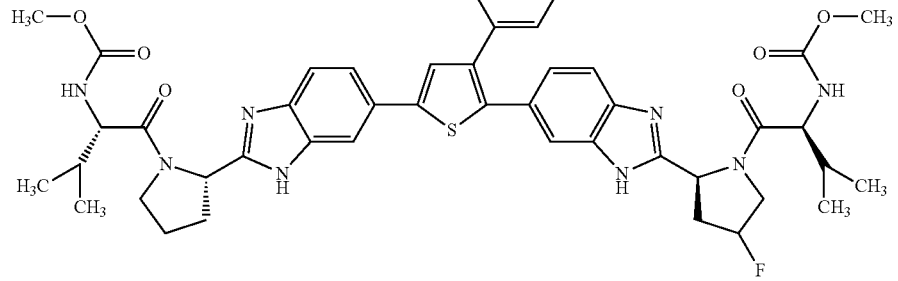
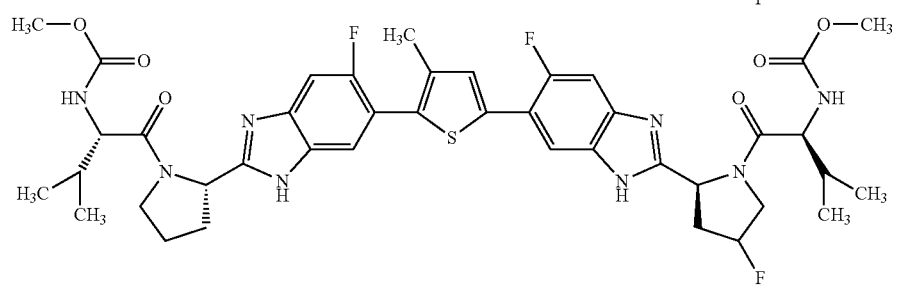
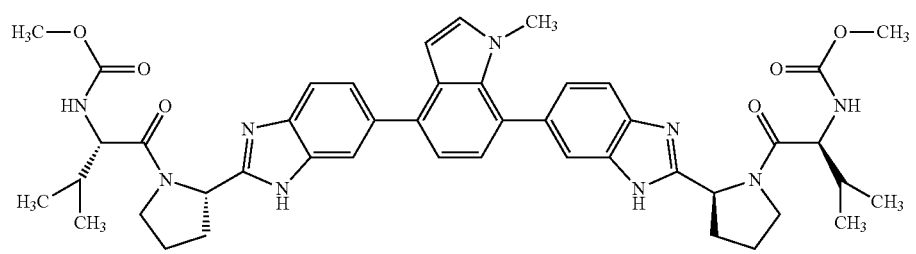
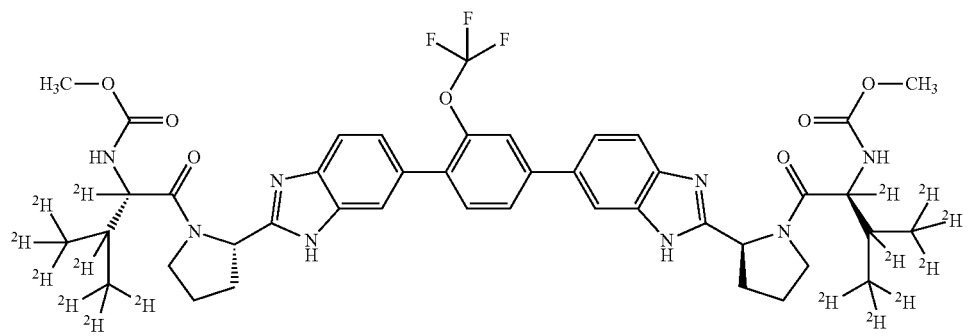
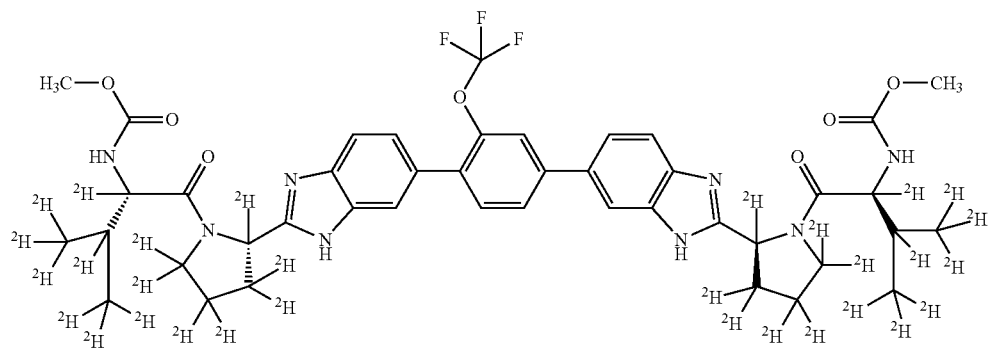

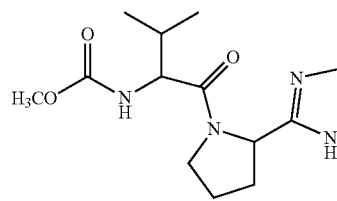
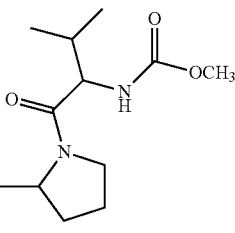
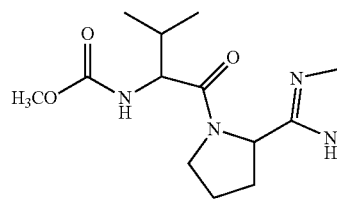
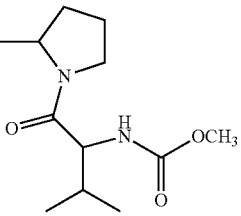
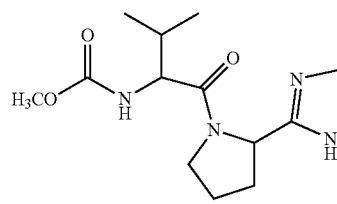
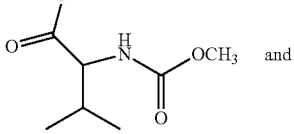 and
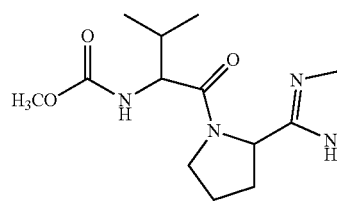
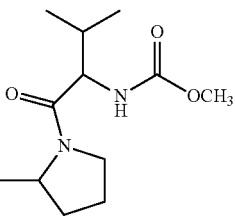

or a pharmaceutically acceptable salt thereof.

11. A pharmaceutical composition comprising an effective amount of the compound of claim 1 or a pharmaceutically acceptable salt thereof, and at least one pharmaceutically acceptable carrier.

12. The pharmaceutical composition of claim 11, further comprising at least one additional therapeutic agent, wherein the additional therapeutic agent(s) is selected from: an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a viral polymerase inhibitor, a virion production inhibitor, a viral entry inhibitor and a viral assembly inhibitor.

13. A method for treating HCV infection in a patient, the method comprising administering to the patient an effective amount of the compound of claim 1 or a pharmaceutically acceptable salt thereof.

14. The method of claim 13, further comprising administering to the patient at least one additional therapeutic agent, wherein the additional therapeutic agent(s) is selected from: an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a viral polymerase inhibitor, a virion production inhibitor, a viral entry inhibitor, and a viral assembly inhibitor.

* * * * *

SEQUENCE LISTING

```
<160> NUMBER OF SEQ ID NOS: 3

<210> SEQ ID NO 1
<211> LENGTH: 17
<212> TYPE: DNA
<213> ORGANISM: Artificial Sequence
<220> FEATURE:
<223> OTHER INFORMATION: 5B.2F Primer

<400> SEQUENCE: 1
atggacaggc gccctga                                                17

<210> SEQ ID NO 2
<211> LENGTH: 20
<212> TYPE: DNA
<213> ORGANISM: Artificial Sequence
<220> FEATURE:
<223> OTHER INFORMATION: 5B.2R Primer

<400> SEQUENCE: 2
ttgatgggca gcttggtttc                                             20

<210> SEQ ID NO 3
<211> LENGTH: 17
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (1)..(1)
<223> OTHER INFORMATION: FAM labeled

<400> SEQUENCE: 3
cacgccatgc gctgcgg                                                17
```